US009955701B2

(12) United States Patent
Errakhi et al.

(10) Patent No.: US 9,955,701 B2
(45) Date of Patent: May 1, 2018

(54) AGRICULTURAL USES OF A NOVEL BACTERIUM OF THE GENUS *STREPTOMYCES*

(71) Applicants: AGRONUTRITION, Carbonne (FR); CENTRE NATIONAL DE LA RECHERCHE SCIENTIFIQUE (C.N.R.S.), Paris (FR); UNIVERSITE PAUL SABATIER TOULOUSE III, Toulouse (FR)

(72) Inventors: Rafik Errakhi, Ben Guerir (MA); Faouzi Attia, Toulouse (FR); Cedric Cabanes, Pechabou (FR); Bernard Dumas, Montrabe (FR); Sophie Vergnes, Saint Sauveur (FR)

(73) Assignees: AGRONUTRITION, Carbonne (FR); CENTRE NATIONAL DE LA RECHERCHE SCIENTIFIQUE (C.N.R.S.), Paris (FR); UNIVERSITE PAUL SABATIER TOULOUSE III, Toulouse (FR)

( * ) Notice: Subject to any disclaimer, the term of this patent is extended or adjusted under 35 U.S.C. 154(b) by 0 days. days.

(21) Appl. No.: 15/023,928

(22) PCT Filed: Sep. 24, 2014

(86) PCT No.: PCT/FR2014/052388
§ 371 (c)(1),
(2) Date: Mar. 22, 2016

(87) PCT Pub. No.: WO2015/044585
PCT Pub. Date: Apr. 2, 2015

(65) Prior Publication Data
US 2016/0255842 A1   Sep. 8, 2016

(30) Foreign Application Priority Data

Sep. 24, 2013 (FR) ...................... 13 59181

(51) Int. Cl.
A01N 63/00 (2006.01)
A01N 63/02 (2006.01)
C05F 11/08 (2006.01)
C12R 1/465 (2006.01)

(52) U.S. Cl.
CPC ............. *A01N 63/00* (2013.01); *A01N 63/02* (2013.01); *C05F 11/08* (2013.01); *C12R 1/465* (2013.01)

(58) Field of Classification Search
None
See application file for complete search history.

(56) References Cited

U.S. PATENT DOCUMENTS

2013/0059729 A1   3/2013 Lebrihi et al.

FOREIGN PATENT DOCUMENTS

| DE | 103 24 193 A1 | 12/2004 |
|---|---|---|
| KR | 2010-0055364 A | 5/2010 |
| WO | 2009/156687 A2 | 12/2009 |
| WO | 2009/156688 A2 | 12/2009 |
| WO | 2012/016140 A2 | 2/2012 |

OTHER PUBLICATIONS

Gopalakrishnan et al., "Evaluation of *Streptomyces* strains isolated from herbal vermicompostfor their plant growth-promotion traits in rice", Microbiological Research, ePub Sep. 2013, vol. 169, pp. 40-48.*
Database EMBL [online] Jan. 31, 2013 (Jan. 31, 2013), "*Streptomyces* sp. AgN23 16S ribosomal RNA gene, partial sequence.", XP002722625, retrieved from EBI accession No. EMBL:JN104730 Database accession No. JN104730 sequence.
Hye Yoon Kim et al: "Identification of antifungal niphimycin from *Streptomyces* sp. KP6107 by screening based on adenylate kinase assay", Journal of Basic Microbiology, vol. 53, No. 7, Jul. 23, 2013 (Jul. 23, 2013), pp. 581-589, XP055111207, ISSN: 0233-111X, DOI: 10.1002/jobm.201200045 p. 581-585.
Database EMBL [Online] May 15, 2011 (May 15, 2011), "*Streptomyces hygroscopicus* subsp. enhygrus strain KP6107 16S ribosomal RNA gene, partial sequence.", XP002722624, retrieved from EBI accession No. EMBL:HQ441251 Database accession No. HQ441251 sequence.
Souad Loqman et al: "*Antagonistic actinomycetes* from Moroccan soil to control the grapevine gray mold", World Journal of Microbiology and Biotechnology, Kluwer Academic Publishers, DO, vol. 25, No. 1, Oct. 4, 2008 (Oct. 4, 2008), pp. 81-91, XP019650434, ISSN: 1573-0972 p. 83-p. 85.
S Srividya et al: "*Streptomyces* sp. 9p as effective biocontrol against chilli soilborne fungal phytopathogens", European Journal of Experimental Biology, vol. 2, No. 1, 2012, pp. 163-173, XP055111252, p. 171.
S. Loqman et al: "*Streptomyces thinghirensis* sp. nov., isolated from rhizosphere soil of *Vitis vinifera*", International Journal of Systematic and Evolutionary Microbiology, vol. 59, No. 12, Jul. 30, 2009 (Jul. 30, 2009), pp. 3063-3067, XP055164561, ISSN: 1466-5026, DOI: 10.1099/ijs.0.008946-0 p. 3064-p. 3066.

(Continued)

Primary Examiner — Michelle F. Paguio Frising
(74) Attorney, Agent, or Firm — Young & Thompson

(57) ABSTRACT

A method for processing plant matter, which involves applying a processing composition including at least one biological agent selected from: bacteria including a DNA sequence, referred to as 16S rDNA, coding for the 16S ribosomal RNA of the bacterium, which is 100% homologous with SEQ ID NO. 1, culture media in which bacteria have grown which include the 16S rDNA sequence that is 100% homologous with SEQ ID NO. 1 and which are substantially free of the bacteria, the culture media including polynucleotides having a DNA sequence which is 100% homologous with SEQ ID NO. 1, and in which the bacteria are selected from bacteria that are consistent with the strain filed and registered on 7 Apr. 2011 with number 1-4467 before the French National Collection of Microorganism Cultures (CNCM) of the Pasteur Institute, and mutant bacteria of the filed strain.

16 Claims, 6 Drawing Sheets

(56) References Cited

OTHER PUBLICATIONS

Q. Tu et al: "Strain/Species-Specific Probe Design for Microbial Identification Microarrays", Applied and Environmental Microbiology, vol. 79, No. 16, Jun. 7, 2013 (Jun. 7, 2013), pp. 5085-5088, XP055111359, ISSN: 0099-2240, DOI: 10.1128/AEM.01124-13 p. 5085.

Mika T. Tarkka et al: "Plant behavior upon contact with *Streptomycetes*", Plant Signaling & Behavior, vol. 3, No. 11, Nov. 2008 (Nov. 2008), pp. 917-919, XP055164498, DOI: 10.4161/psb. 5996 p. 917; figure 2.

International Search Report, dated Feb. 18, 2015, from corresponding PCT Application.

\* cited by examiner

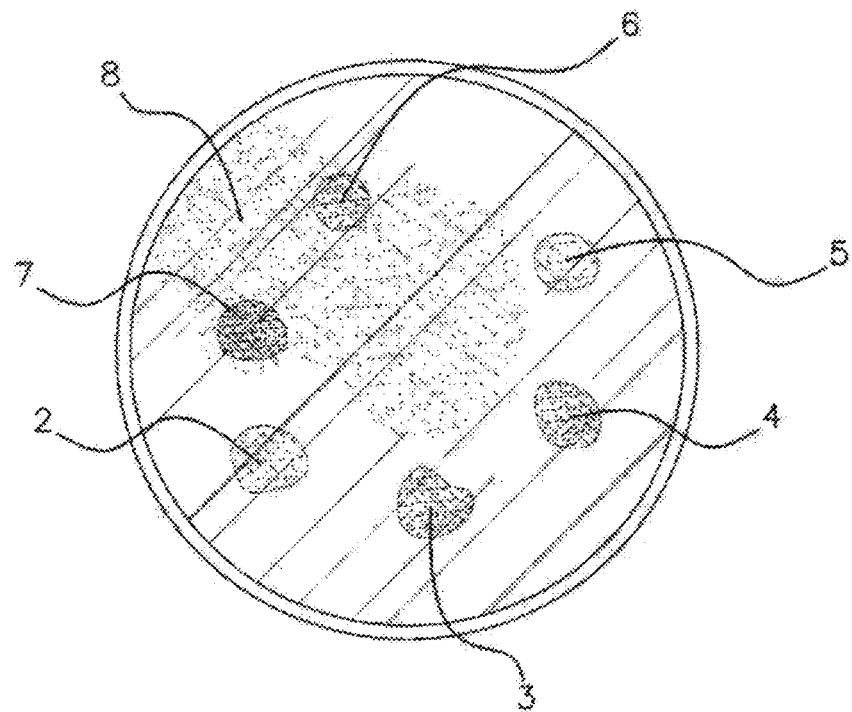
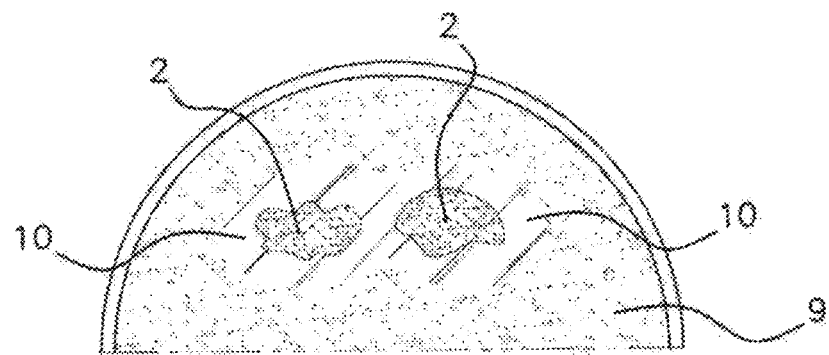

a                b c                d

A
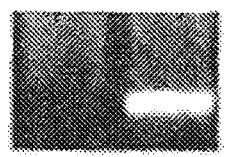
1    2
B
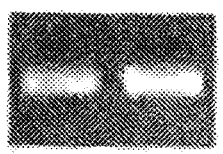
3    4
C
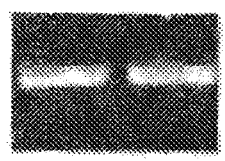
5    6
Fig 7

SEQUENCE LISTING

<160> NUMBER OF SEQ ID NOS: 12

<210> SEQ ID NO 1
<211> LENGTH: 1336
<212> TYPE: DNA

```
<213> ORGANISM: Streptomyces
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1049)..(1049)
<223> OTHER INFORMATION: n is a, c, g, or t

<400> SEQUENCE: 1
tagtggcgaa cgggtgagta acacgtgggc aatctgccct gcactctggg acaagccctg      60
gaaacggggt ctaataccgg atatgacacg ctcccgcatg ggatgcgtgt ggaaagctcc     120
ggcggtgcag gatgagcccg cggcctatca gcttgttggt ggggtgatgg cctaccaagg     180
cgacgacggg tagccggcct gagagggcga ccggccacac tgggactgag acacggccca     240
gactcctacg ggaggcagca gtggggaata ttgcacaatg ggcgaaagcc tgatgcagcg     300
acgccgcgtg agggatgacg gccttcgggt tgtaaacctc tttcagcagg gaagaagcga     360
gagtgacggt acctgcagaa gaagcgccgg ctaactacgt gccagcagcc gcggtaatac     420
gtagggcgca agcgttgtcc ggaattattg ggcgtaaaga gctcgtaggc ggcttgtcgc     480
gtcggatgtg aaagcccggg gcttaacccc gggtctgcat tcgatacggg caggctagag     540
ttcggtaggg gagatcggaa ttcctggtgt agcggtgaaa tgcgcagata tcaggaggaa     600
caccggtggc gaaggcggat ctctgggccg atactgacgc tgaggagcga aagcgtgggg     660
agcgaacagg attagatacc ctggtagtcc acgccgtaaa cgttgggaac taggtgtggg     720
cgacattcca cgtcgtccgc gccgcagcta acgcattaag ttccccgcct ggggagtacg     780
gccgcaaggc taaaactcaa aggaattgac ggggggcccg cacaagcggc ggagcatgtg     840
gcttaattcg acgcaacgcg aagaacctta ccaaggcttg acatacaccc ggaaacctct     900
ggagacaggg gccccccttg tggtcggtgt acaggtggtg catggcttgt cgtcagctcg     960
tgtcgtgaga tgttgggtta agtccccgca acgagcgcaa cccttgttct gtgttgccag    1020
catgcctttc ggggngtgat ggggacttnc acaggagact gccggggtca actcggagga    1080
aggtggggac gacgtcaagt catcatgccc cttatgtctt gggctgcaca cgtgctacaa    1140
tggccggtac aatgagctgc gaagccgtga ggtggagcga atctcaaaaa gccggtctca    1200
gttcggattg ggtctgcaa ctcgacccca tgaagtcgga gtcgctagta atcgcagatc    1260
agcattgctg cggtgaatac gttcccgggc cttgtacaca ccgcccgtca cgtcacgaaa    1320
gtcggtaaca cctgaa                                                    1336

<210> SEQ ID NO 2
<211> LENGTH: 20
<212> TYPE: DNA
<213> ORGANISM: Artificial Sequence
<220> FEATURE:
<223> OTHER INFORMATION: Universal primer 27F

<400> SEQUENCE: 2
agagtttgat cctggctcag                                                  20

<210> SEQ ID NO 3
<211> LENGTH: 19
<212> TYPE: DNA
<213> ORGANISM: Artificial Sequence
<220> FEATURE:
<223> OTHER INFORMATION: Universal primer 1492R

<400> SEQUENCE: 3
```

```
ggttaccttg ttacgactt                                                    19
```

<210> SEQ ID NO 4
<211> LENGTH: 24
<212> TYPE: DNA
<213> ORGANISM: Artificial Sequence
<220> FEATURE:
<223> OTHER INFORMATION: Specific primer PR-1F

<400> SEQUENCE: 4

```
ctggctattc tcgatttta atcg                                               24
```

<210> SEQ ID NO 5
<211> LENGTH: 24
<212> TYPE: DNA
<213> ORGANISM: Artificial Sequence
<220> FEATURE:
<223> OTHER INFORMATION: Specific primer PR-1R

<400> SEQUENCE: 5

```
tcctgcatat gatgctcctt attg                                              24
```

<210> SEQ ID NO 6
<211> LENGTH: 24
<212> TYPE: DNA
<213> ORGANISM: Artificial Sequence
<220> FEATURE:
<223> OTHER INFORMATION: Primer EF1F

<400> SEQUENCE: 6

```
atgccccagg acatcgtgat ttca                                              24
```

<210> SEQ ID NO 7
<211> LENGTH: 24
<212> TYPE: DNA
<213> ORGANISM: Artificial Sequence
<220> FEATURE:
<223> OTHER INFORMATION: Primer EF1R

<400> SEQUENCE: 7

```
ttggcggcac ccttagctgg atca                                              24
```

<210> SEQ ID NO 8
<211> LENGTH: 3483
<212> TYPE: DNA
<213> ORGANISM: Streptomyces

<400> SEQUENCE: 8

```
ttggccgcct cgcgcaacgc ctcgactgcc aatacgaaca atggcgccag caccgccccg       60
ctgcgcatct cctttgcgaa gatcaggag cctctcgagg ttccgaacct cctcgcgctg       120
cagaccgaga gcttcgattg gctgctcggc aatgccgcct ggaaggctcg cgtcgaggct      180
gcgctggaca gcggtcagga cgtccccacc aagtccggtc tggaagagat cttcgaggag     240
atctccccga tcgaggactt ctccgggtcg atgtccctga ctttccgtga tcaccgtttc     300
gagccgccga agaactcgat cgacgagtgc aaggagcgtg acttcaccta cgccgctccg     360
ctcttcgtca cggccgagtt caccaacaac gagaccggcg agatcaagtc ccagacggtc     420
ttcatgggcg acttcccgct catgaccgac aagggcacct tctgcatcaa cggcaccgag     480
cgtgtcgtcg tctcgcagct ggtccgctcg ccgggtgtct acttcgactc ctccatcgac     540
aagacgtccg acaaggacat cttctccgtc aaggtcatcc cgtcccgggg tgcctggctg     600
```

```
gagatggaga tcgacaagcg tgacatggtc ggtgtgcgta tcgaccgcaa gcgcaagcag    660
tccgtcaccg ttctcctgaa ggctctcggc tggacgaccg agcagatcct ggaggagttc    720
ggcgagtacg agtcgatgcg cgccaccctg gagaaggacc acacccaggg ccaggacgac    780
gcgctgctcg acatctaccg caagctgcgt ccgggcgagc cccccacacg ggaggccgcg    840
cagacgctgc tcgagaacct ctacttcaac ccgaagcgct acgacctcgc gaaggtcggc    900
cgctacaagg tcaacaagaa gctgggttcg ccgctccgc tggacgcggg cgtcctgacg    960
gtcgaggacg tcatcgcctc gatcaagtac ctggtgaagc tgcacgccgg tgagaccgag   1020
accgtcgggg acaacggcca gtccgtggtc gtcgagaccg acgacatcga ccacttcggc   1080
aaccgccgta tccgtaacgt cggcgagctg atccagaacc aggtccgcac gggtctggcc   1140
cgtatggagc gcgtcgtgcg tgagcgcatg acgactcagg acgtcgaggc gatcacgccg   1200
cagaccctga tcaacatccg gccggtcgtc gcctccatca aggagttctt cggcaccagc   1260
cagctgtcgc agttcatgga ccagacgaac ccgctgtcgg gtctgaccca caagcgccgt   1320
ctgaacgcgc tcggccccgg tggtctctcc cgtgagcggg cgggcttcga ggtccgtgac   1380
gtgcacccgt cgcactacgg ccgcatgtgc ccgatcgaga cgcccgaagg cccgaacatc   1440
ggtctgatcg gctcgctcgc ctcgtacggc cgggtcaacg cgttcggttt catcgagacc   1500
ccgtaccgca aggtcgtcga cggtgtcgtc accgacgacg tcgactacct gacggccgat   1560
gaagaggacc gcttcgtcat cgcgcaggcc aacgccccgc tcgcggacga cctgcgcttc   1620
gccgagaacc gcgtcctggt ccgccgccgt ggcggcgagg tcgactacat ccccggcgac   1680
gacgtcgact acatggacgt ctcaccgcgc cagatggtgt cggtcgcgac cgcgatgatc   1740
cccttcctcg agcacgacga cgccaaccgc gcgctcatgg gctcgaacat gatgcgccag   1800
gccgtgccgc tgatcaaggc ggagtccccg ctggtcggca ccggcatgga gtaccgctgt   1860
gcggtcgacg ccggcgacgt catcaaggcc gagaaggacg tgtcgtcca ggaggtctcc   1920 gccgactacg tgacggtggc caacgacgac ggcacctaca ccacctaccg ggtggccaag   1980
ttctcccgct ccaaccaggg cacctccttc aaccagaagg tcgtcgtgga cgagggtgcg   2040
cgggtgatcg ccggccaggt gctggccgac ggcccgtcca ccgaggacgg cgagatggcg   2100
ctcggcaaga acctcctggt ggcgttcatg ccgtgggagg ccacaacta cgaggacgcg   2160 atcatcctca gccagcgtct ggtgcaggac gacgtcctct cctcgatcca catcgaggag   2220
cacgaggtcg atgcccgtga caccaagctc ggccccgagg agatcacccg ggacatcccg   2280
aacgtctccg aggaggtcct cgccgacctc gacgagcgcg gcatcatccg gatcggtgcc   2340
gaggtcgtcg ccggcgacat cctggtcggc aaggtcaccc cgaagggcga gaccgagctg   2400
accccggagg agcggctgct cgcgcgcgatc ttcggtgaga aggcccgtga ggtccgtgac   2460
acctcgctga aggtgccgca cggtgagatc ggcaaggtca tcggcgtccg cgtcttcgac   2520
cgcgaagagg cgacgaact gccgccgggc gtgaaccagc tggtccgcgt ctacgtggcg   2580
cagaagcgca agatcaccga tggtgacaag ctcgccggcc gtcacggcaa caagggcgtc   2640
atctccaaga tcctgccggt cgaggacatg ccgttcctgg aggacggcac cccggtcgac   2700
atcatcctca acccgctggg tgtcccgtcc gaatgaacc cgggacaggt cctggagatc   2760
cacctgggct ggctggcctc ccgcggctgg aaggtcgagg gctccgagga ctggatgcag   2820
cggctccagg ccatcggcgc cgacgaggtc gagcccggca ccaacgtcgc gaccccggtc   2880
ttcgacggcg cccgcgagga cgagatcgcc ggtctcttcg actcgacgat cccgaaccgc   2940
gacggcgacc gcctggtcca gtcgtccggc aaggcccggc tcttcgacgg ccgctccggc   3000
```

-continued

```
gagccgttcc cggagccgat ctcggtcggc tacatgtaca tcctcaagct gcaccacctg    3060
gtggacgaca agctgcacgc ccggtccacc ggtccgtact cgatgatcac ccagcagccg    3120
ctgggtggta aggctcagtt cggtggccag cgcttcggtg agatggaggt gtgggcgctg    3180
gaggcttatg cgccgcgta cgccctccag gagctgctga ccatcaagtc cgacgacgtg    3240
accggccgcg tgaaggtcta cgaggccatc gtcaagggcg agaacattcc cgagcccggc    3300
atccccgagt ccttcaaggt gctcatcaag agatgcagt ccctgtgcct caacgtggag    3360
gtgctgtcgt ccgacggcat gtccatcgag atgcgcgaca ccgacgagga cgtcttccgc    3420
gctgcggagg agctcggtat cgacctgtcc cggcgcgagc cgagcagcgt cgaagaggtc    3480
tga                                                                  3483
```

<210> SEQ ID NO 9
<211> LENGTH: 2031
<212> TYPE: DNA
<213> ORGANISM: Streptomyces

<400> SEQUENCE: 9

```
gtgctgtgcc agaaagggcg cttcgtggcc gattccggca accccatcga aaacatcccg     60
tccacgcccg acgacgaggc cctggctccg ccgtcgtacg acgccagtgc gattaccgtc    120
ctggaagggc tggaggcggt ccgcaagcga cccggtatgt acatcggttc caccggtgag    180
cgcggcctgc accatctcgt ccaagaggtc gtcgacaact ccgtcgacga ggccatggcc    240
ggtcacgcgg acagcatcga ggtcacgatc ctcgccgacg cgggcgtccg cgtcgtggac    300
aacggccgcg ggatcccggt gggcatcgtc ccctcggagg ggaagccggc tgtggaggtc    360
gtgctgaccg tgctgcacgc gggcggcaag ttcggcggcg cgggctacgc cgtctccggc    420
ggtctgcacg gcgtcggcgt ctccgtcgtc aacgccctgt cctcgaaggt gtcggtcgag    480
gtcaagacgg acggctaccg ctggacccag gactacaaga cgggagcgcc gaccgcgccc    540
ctggcccgga acgaggccac ggaggagacc ggcaccacgg tcaccttctg ggcggacccg    600
gacgtcttcg agaccaccga gtactccttc gagacgctgg cccggcgctt ccaggagatg    660
gcgttcctca acaagggcct gtcgatctcg ctcaaggacg agcgcgaggc ccatgtggac    720
gaggagggca agccgctctc cgtgaagtac cactacgagg gcggcatcgt cgacttcgtg    780
acctacctca actcccgcaa gggcgagctg gtccacccca cggtgatcgg gttcgaggcc    840
gaggacaagg agcggatgct ctccctcgag atcgcgatgc agtggaacac ccagtacacc    900
gagggtgtct acagcttcgc gaacaccatc cacacccatg agggcggcac ccacgaggag    960
ggcttccgcg ccgcgctgac gtacctgatc aacaagtacg cgcgcgacaa gaagctgctc   1020
cgggagcgtg acgacaacct caccggtgag gacatccgcg agggcctgac cgccatcatc   1080
tcggtcaagc tgggcgagcc gcagttcgag ggccagacca agaccaagct gggcaacacg   1140
gaggccaaga ccttcgtcca gaagatcgtc aacgagcatc tcgccgactg gctgaccgt    1200 aaccctaatg aggcggcgga catcgtccgc aaggggatcc aggcggcgac ggccgcggtc   1260
gcggcccgta aggcgcggga tctgacccgc cgtaaggggc tgctggagac cgcgtcgctg   1320
ccgggcaagc tgagcgactg ccagtccaat gacccgtcga agtgcgagat cttcatcgtc   1380
gagggtgact ccgccggcgg ctcggccaag tccgccgtca cccgcagta tcaggcgatc   1440 ctcccgatcc gcggcaagat cctcaacgtg gagaaggccc gggtcgacaa gatcctgcag   1500
aacaacgagg tccaggcgct gatctccgcc ttcggcaccg gggtgcacga ggacttcgac   1560
```

| | |
|---|---|
| atcgccaagc tccgctatca caagatcatt ctgatggcgg acgccgatgt cgacggccag | 1620 |
| cacatcaaca ccctgctgct gaccttcctc ttccgcttca tgcgcccgct ggtcgaggcg | 1680 |
| gggcatgtct tcctctcccg tccgccgctc tacaagatca agtggggccg ggacgacttc | 1740 |
| gagtacgcgt actcggaccg ggagcgggac gcgctgatcc aggtcggccg tgaacagggc | 1800 |
| aagcgcatca gggacgactc ggtccagcgc ttcaagggtc tgggcgagat gaacgccgaa | 1860 |
| gagctgcggg tcaccacgat ggaccccgac caccgcgtcc tgggccaggt caccctggac | 1920 |
| gacgcggcgc aggccgacga cctgttctcg gtcctgatgg gtgaggacgt cgaggcacgg | 1980 |
| cgctcgttca tccagcgcaa cgccaaggat gtccgcttcc tcgacatctg a | 2031 |

<210> SEQ ID NO 10
<211> LENGTH: 990
<212> TYPE: DNA
<213> ORGANISM: Streptomyces

<400> SEQUENCE: 10

| | |
|---|---|
| ggcgatcggc cgaacgagcc ggtcgaggtc atccccaccg ggtcgaccgc tctcgacgtc | 60 |
| gccctcggcg tcggcggtct gccgcgcggc cgggtggtcg aggtctacgg ccccgagtcc | 120 |
| tccggtaaga cgaccctgac cctgcacgcg gtggccaatg cccagcgggc cggcggcacc | 180 |
| gttgccttcg tggacgccga gcacgccctc gaccctgact acgcgcagaa gctgggcgtg | 240 |
| gacaccgact ccctgatcct gtcccagccg acaacggcg agcaggcgct cgagatcgtg | 300 |
| gacatgctgg tccgctccgg cgccctcgac ctcatcgtca tcgactccgt cgccgccctg | 360 |
| gtgccgcgcg cggagatcga gggcgagatg ggcgactccc acgtcggcct ccaggcccgg | 420 |
| ctgatgagcc aggcgctccg taagatcacc agcgcgctca accagtccaa gaccaccgcg | 480 |
| atcttcatca accagctccg cgagaagatc ggcgtgatgt tcggctcgcc ggagaccacg | 540 |
| accggtggcc gggcgctgaa gttctacgcg tcggtgcgca tcgacatccg ccgcatcgag | 600 |
| accctcaagg acggcaccga cgcggtcggc aaccgcaccc gcgtcaaggt cgtcaagaac | 660 |
| aaggtcgcgc gcccctcaa gcaggccgag ttcgacatcc tctacggcca gggcatcagc | 720 |
| cgtgagggcg gtctgatcga catgggcgtc gagcacggct tcgtccgcaa gtccggtgcc | 780 |
| tggtacacct acgagggcga ccagctcggc cagggcaagg agaacgcccg caacttcctg | 840 |
| aaggacaacc ccgatctcgc caatgagatc gagaagaaga tcaaggaaaa gctcggcatc | 900 |
| ggggtgaggc cccaggaccc ggcggccgcg gcacccacca cggacgcggc tggtgccgcg | 960 |
| ggcgtgaccg acgccgcacc ggcgaaggcc | 990 |

<210> SEQ ID NO 11
<211> LENGTH: 1209
<212> TYPE: DNA
<213> ORGANISM: Streptomyces

<400> SEQUENCE: 11

| | |
|---|---|
| gtgcccagcg ccgagggcta tttcggcgcc ttcggcggca agttcatccc cgaggcgctc | 60 |
| gtcgccgccg tcgacgaggt cgcggccgag tacgagaagg ccaagacgga ccccgccttc | 120 |
| gcggccgagc tcgaggatct gctggtcaac tacaccggcc ggcccagtgc gctgaccgag | 180 |
| gtgcggcggt tcgccgagca cgccgggggc gcccgggtct tcctcaagcg ggaggacctc | 240 |
| aaccacaccg gctcccacaa gatcaacaat gtgctggggc aggccctgct caccaagcgc | 300 |
| atgggcaagt cccgggtcat cgccgagacc ggcgccggtc agcacggcgt ggccacggcc | 360 |
| accgcatgtg cgctgttcgg gctcgaatgc accatctaca tgggcgaggt cgacacccag | 420 |

| | |
|---|---|
| cggcaggcgc tcaatgtggc gcggatgcgg atgctgggcg ccgaggtcat ctccgtgacc | 480 |
| tccggcagcc gcaccctgaa ggacgccatc aacgaggcgt tccgggactg ggtcgccaat | 540 |
| gtggaccgca cccactacct cttcggtacg gtggccggcc cccacccctt cccggcgctg | 600 |
| gtgcgcgact tccaccgggt gatcggcgtg gaggcgcggc ggcagatcct ggagcggacc | 660 |
| gggcggctgc cggacgcggt cgcggcctgt gtgggcggcg gatccaacgc gatcgggctg | 720 |
| ttccacgcct tcctgccgga cgagagcgtg cgcctcgtcg gcttcgagcc cgccggacac | 780 |
| ggtgtggaga ccggggagca cgcggccacg ctgagccagg gcgagcccgg gatcctgcac | 840 |
| ggctcccggt cgttcgtgct ccaggacgag gacggccaga tcaccgagcc gtactcgatc | 900 |
| tcggccggtc tcgactaccc cggcgtcggg ccggagcacg cgtatctgaa ggacatcggc | 960 |
| cgtgccgagt accgggcggt caccgacgac gaggcgatgc gggcgctgcg gctgctctcg | 1020 |
| gagaccgagg gcatcatccc ggcgatcgag agcgcccacg cgctggcggg cgccctggac | 1080 |
| ctcggccgtg agctggggag cgacggcctg gtgctggtca acctctccgg gcgcggcgac | 1140 |
| aaggacatgg acacggcggc tcggtacttc gggctctacg accagcagag cgaccaggga | 1200 |
| gcgaagtga | 1209 |

<210> SEQ ID NO 12
<211> LENGTH: 1419
<212> TYPE: DNA
<213> ORGANISM: Streptomyces

<400> SEQUENCE: 12

| | |
|---|---|
| gtggcctccg gccgcgtcgc gcgggtcatc ggcccggtcg tcgacgtgga gttccccgtc | 60 |
| gacgcgatgc cggagatcta caacgcgctg caggtcgagg tcgccgaccc ctcccaggag | 120 |
| ggggcgaaga agaccctgac cctcgaggtc gcccagcacc tcggcgaggg cctggtccgc | 180 |
| gccatctcca tggagcccac cgacggcctg gtccgccagg ccgcggtgac cgacaccggc | 240 |
| gacggcatca cggtgccggt cggcgatgtc accaagggcc gggtgttcaa caccctcggc | 300 |
| aagatcctca cgagcccga ggccgagtcc gaggtcaccg agcgctggtc catccaccgc | 360 |
| aaggccccgg ccttcgacca gctcgagtcc aagaccgaga tgttcgagac cggcctgaag | 420 |
| gtcgtcgacc tgctgacccc gtacgtcaag ggcggcaaga tcggtctgtt cggcggcgcg | 480 |
| ggcgtcggca agaccgtgct catccaggaa atgatcatgc gtgtggccaa gctgcacgag | 540 |
| ggcgtttccg tgttcgccgg tgtcggcgag cgcacccgtg agggcaacga cctgatcgag | 600 |
| gagatggccg agtccggcgt gctcccgcag accgcgctgg tcttcggcca gatggatgag | 660 |
| cccccgggca cccgtctgcg cgtcgccctg gccggtctga ccatggcgga gtacttccgc | 720 |
| gatgtgcaga agcaggacgt gctgttcttc atcgacaaca tcttccgctt cacccaggcc | 780 |
| ggttccgagg tctcgaccct gctcggccgg atgccctccg cggtgggcta ccagccgaac | 840 |
| ctggccgaca gatgggcat cctgcaggag cgcatcacct cgaccgtgg tcactcgatc | 900 |
| acctcgatgc aggcgatcta cgtccccgcg gacgacctga ccgacccggc cccggcgacc | 960 |
| accttcgcgc acctcgacgc gaccacggtg ctctcccggc cgatctcgga aagggcatc | 1020 |
| tacccggcgg tggacccgct ggactcgacg tcccggatcc tggacccgcg ctacatctcg | 1080 |
| caggagcact acgactgcgc ctcgcgcgtg aagtcgatcc tgcagaagta caaggacctc | 1140 |
| caggacatca tcaacatcct gggcatcgac gagctcggcg aggaggacaa gctcaccgtc | 1200 |
| ttccgcgccc gccggatcga gcgcttcctg tcgcagaaca cccacgcggc gaagcagttc | 1260 |

-continued

```
accggcctcg acggatcgga tgtgccgctg gacgagtcca tcgccgcgtt caacgcgatc    1320
gccgatggtg agttcgacca cttccccgag caggcgttct tcatgtgcgg tggcctggac    1380
gacctcaagg ccaaggccaa ggagctgggc gtctcctga                           1419
```

AGRICULTURAL USES OF A NOVEL BACTERIUM OF THE GENUS *STREPTOMYCES*

FIELD OF THE INVENTION

The invention relates generally to agricultural uses of a novel bacterium of the genus *Streptomyces*. The invention relates in particular to a method for treating plants, to a treatment composition for plants and to uses of such a treatment composition for the treatment of plants.

BACKGROUND OF THE INVENTION

The development of intensive agricultural plant crops is today necessary in order to meet the world's food needs. To that end, such intensive agricultural plant crops require the use of agents which are capable of optimising the growth of the valuable plants and of minimising the growth of undesirable plants and/or pathogenic agents. There are known in particular agents which aim to improve the nutrition of the plants and agents for protecting the plants from pathogenic organisms, especially from phytopathogenic bacteria and/or from fungi, which are liable to affect the optimum growth of the plants.

Products for fertilising the soil are also known. They are generally fertilisers obtained from the chemical industry, which are often in a solid form which is sparingly soluble in the soil, and consequently they have to be applied in massive doses at the precise moment at which such fertilisation products are necessary for the optimum growth of the plants. The excess of such solid fertilisation products which are applied to the soil and not taken up by the plants remains in the soil for a time and is gradually dissolved by rainwater or by watering, before reaching water bodies and polluting them.

Solutions for improving the fertilisation of the soil without polluting the environment and in particular water bodies while promoting the nutrition and growth of the plants are therefore desirable.

Accordingly, the invention aims to provide a solution to this problem.

Moreover, many phytopathogenic agents are liable to develop in plant crops and at the expense thereof, reducing the production yield thereof and the quality of the plant production.

Accordingly, the invention aims also to provide a solution for protecting plants from certain phytopathogenic organisms—bacteria and/or fungi.

SUMMARY OF THE INVENTION

To that end, the invention relates to a method for treating plant material, wherein there is applied a treatment composition comprising at least one biological agent chosen from the group formed of:

bacteria comprising a DNA sequence, named 16S rDNA, which codes for the 16S ribosomal RNA of said bacterium and is 100% homologous with SEQ ID_NO1, culture media in which bacteria comprising the 16S rDNA sequence that is 100% homologous with SEQ ID_NO1 have developed and which are substantially free of said bacteria, said culture media comprising polynucleotides having a DNA sequence that is 100% homologous with SEQ ID_NO1, and wherein the bacteria are chosen from the group formed of bacteria corresponding to the strain deposited and registered on 7 Apr. 2011 under number I-4467 with the National Collection of Microorganisms Cultures (CNCM) of the Pasteur Institute, and mutant bacteria of that deposited strain.

Sequence SEQ ID_NO1 is described hereinbelow:

```
tagtggcgaa cgggtgagta acacgtgggc aatctgccct gcactctggg acaagccctg    60
gaaacggggt ctaataccgg atatgacacg ctcccgcatg ggatgcgtgt ggaaagctcc   120
ggcggtgcag gatgagcccg cggcctatca gcttgttggt ggggtgatgg cctaccaagg   180
cgacgacggg tagccggcct gagagggcga ccggccacac tgggactgag acacggccca   240
gactcctacg ggaggcagca gtggggaata ttgcacaatg ggcgaaagcc tgatgcagcg   300
acgccgcgtg agggatgacg gccttcgggt tgtaaacctc tttcagcagg gaagaagcga   360
gagtgacggt acctgcagaa gaagcgccgg ctaactacgt gccagcagcc gcggtaatac   420
gtagggcgca agcgttgtcc ggaattattg ggcgtaaaga gctcgtaggc ggcttgtcgc   480
gtcggatgtg aaagcccggg gcttaacccc gggtctgcat tcgatacggg caggctagag   540
ttcggtaggg gagatcggaa ttcctggtgt agcggtgaaa tgcgcagata tcaggaggaa   600
caccggtggc gaaggcggat ctctgggccg atactgacgc tgaggagcga aagcgtgggg   660
agcgaacagg attagatacc ctggtagtcc acgccgtaaa cgttgggaac taggtgtggg   720
cgacattcca cgtcgtccgc gccgcagcta acgcattaag ttccccgcct ggggagtacg   780
gccgcaaggc taaaactcaa aggaattgac ggggggcccg cacaagcggc ggagcatgtg   840
gcttaattcg acgcaacgcg aagaacctta ccaaggcttg acatacaccc ggaaacctct   900
ggagacaggg gccccccttg tggtcggtgt acaggtggtg catggcttgt cgtcagctcg   960
tgtcgtgaga tgttgggtta agtccccgca acgagcgcaa cccttgttct gtgttgccag  1020
```

```
                                      -continued
catgcctttc gggggntgat ggggacttnc acaggagact gccggggtca actcggagga 1080
aggtggggac gacgtcaagt catcatgccc cttatgtctt gggctgcaca cgtgctacaa 1140
tggccggtac aatgagctgc gaagccgtga ggtggagcga atctcaaaaa gccggtctca 1200
gttcggattg gggtctgcaa ctcgacccca tgaagtcgga gtcgctagta atcgcagatc 1260
agcattgctg cggtgaatac gttcccgggc cttgtacaca ccgcccgtca cgtcacgaaa 1320
gtcggtaaca cctgaa.                                                1336
```

In the above sequence SEQ ID_NO1, the symbol "n" at positions 1036 and 1049 of sequence SEQ ID_NO1 denotes, according to IUPAC ("*International Union of Pure and Applied Chemistry*"), any one of the four nucleotides a, t, c or g. Accordingly, the nucleotide n at position 1036 is chosen from the group formed of the nucleotide "a", of the nucleotide "t", of the nucleotide "g" and of the nucleotide "c", and the nucleotide n at position 1049 is chosen, independently of the nucleotide at position 1036, from the group formed of the nucleotide "a", of the nucleotide "t", of the nucleotide "g" and of the nucleotide "c".

Accordingly, the invention relates to a method for treating plant material, wherein the treatment composition is applied to at least part of said plant material or to a cultivation substrate of said plant material.

The inventors have observed that, wholly surprisingly and unforeseeably, a treatment composition according to the invention has the ability to inhibit the growth of certain bacteria such as, for example, *Micrococcus luteus*, *Bacillus subtilis* and of certain phytopathogenic bacteria or fungi such as *Streptomyces scabies*, *Botrytis cinerea*, *Fusarium culmorum*, *Pythium ultimum*, *Phaeomoniella chlamydospora*, *Phaeomoniella aelophilum*, *Eutypa lata*, *Fomitiporia mediterranea* and *Botryosphaeria obtusa*.

A strain of bacteria having a DNA sequence that is 100% homologous with SEQ ID_NO1 was deposited by the applicant and registered on 7 Apr. 2011 under number I-4467 with the National Collection of Microorganisms Cultures (CNCM) of the Pasteur Institute (whose address is 25, rue du Docteur Roux, 75724 Paris cedex 15) having the status of international depository authority under the Budapest treaty.

In a treatment method according to the invention there are used bacteria which are of the genus *Streptomyces* and which have a DNA sequence that is 100% homologous with SEQ ID_NO1.

DETAILED DESCRIPTION OF THE INVENTION

Advantageously and according to the invention, the isolated bacterium has a DNA sequence coding for the RNA polymerase beta subunit (polB) which is homologous with SEQ ID_NO8. The isolated bacterium therefore has sequence SEQ ID_NO8 as the sequence coding for the RNA polymerase beta subunit (polB).

Advantageously and according to the invention, the isolated bacterium has a DNA sequence coding for gyrase (gyrB) which is homologous with SEQ ID_NO9. The isolated bacterium therefore has sequence SEQ ID_NO9 as the sequence coding for gyrase (gyrB).

Advantageously and according to the invention, the isolated bacterium has a DNA sequence coding for recombinase (RecA) which is homologous with SEQ ID_NO10. The isolated bacterium therefore has sequence SEQ ID_NO10 as the sequence coding for recombinase (RecA).

Advantageously and according to the invention, the isolated bacterium has a DNA sequence coding for the tryptophan synthase beta subunit (trpB) which is homologous with SEQ ID_NO11. The isolated bacterium therefore has sequence SEQ ID_NO11 as the sequence coding for tryptophan synthase (trpB).

Advantageously and according to the invention, the isolated bacterium has a DNA sequence coding for the ATP synthase beta subunit (AtpB) which is homologous with SEQ ID_NO12. The isolated bacterium therefore has sequence SEQ ID_NO12 as the sequence coding for the ATP synthase beta subunit (AtpB).

Advantageously and according to the invention, the isolated bacterium has at least one of the sequences SEQ ID NO_4, SEQ ID_NO5, SEQ ID_NO6, SEQ ID_NO7 and SEQ ID_NO8. Advantageously and according to the invention, the isolated bacterium has each of the sequences SEQ ID NO_4, SEQ ID_NO5, SEQ ID_NO6, SEQ ID_NO7 and SEQ ID_NO8.

Advantageously and according to the invention, the treatment composition comprises bacteria chosen from the group formed of bacteria corresponding to the strain deposited and registered on 7 Apr. 2011 under number I-4467 with the National Collection of Microorganisms Cultures (CNCM) of the Pasteur Institute and mutant bacteria of that deposited strain comprising a sequence portion that is 100% homologous with sequence SEQ ID_NO1.

In a first variant of a method according to the invention there are used bacteria corresponding to the strain deposited and registered on 7 Apr. 2011 under number I-4467 with the National Collection of Microorganisms Cultures (CNCM) of the Pasteur Institute, such bacteria corresponding to the deposited strain comprising a DNA sequence portion that is 100% homologous with sequence SEQ ID_NO1.

The strain deposited with the CNCM under no. I-4467 forms, when cultivated on ISP-2 medium or on Bennett's solid medium, clusters or bacterial "colonies" exhibits:
- a branched mycelium, named the substrate mycelium, which develops in the thickness of the solid medium and has a colour varying from yellowish-brown to greyish-brown depending on the composition of the solid medium;
- an aerial mycelium which develops at the air/solid interface and is white in colour.

The strain deposited with the CNCM is a strain of bacteria isolated from any natural medium. In particular, the strain deposited with the CNCM has been isolated from a natural original medium in which it pre-existed.

The bacteria of the strain deposited with the CNCM are characterised by all or some of the following features:
- they are non-pathogenic (harmless) to humans;
- they are Gram-positive bacteria;
- they are saprophytic bacteria, that is to say capable of breaking down the organic matter of the soil;

they have an optimum growth temperature of from 12° C. to 37° C., preferably from 28° C. to 30° C.;

they have an optimum growth pH of from 6 to 8;

they are capable of utilising D-glucose, mannitol, lactose, sucrose, maltose and dextrin as a carbon source;

they are not capable of preferentially utilising galactose, inositol, sorbose, fructose, arabinose, raffinose, rhamnose or cellulose as the sole carbon source;

they are capable of utilising amino acids, nitrate salts and ammonium salts as a nitrogen source;

they are capable of reducing nitrates to nitrites and of breaking down adenine, Tween 20 and sodium acetate;

they are not capable of hydrolysing starch and utilising the hydrolysis products.

In a second variant of a method according to the invention there are used mutant bacteria of the bacteria of the strain deposited with the CNCM, that is to say obtained by mutation of the bacteria of the strain deposited with the CNCM, such mutant bacteria comprising a 16S rDNA sequence that is 100% homologous with sequence SEQ ID_NO1.

Such mutant bacteria are obtained by treating bacteria of the strain deposited with the CNCM by any method of mutagenesis, especially chosen from the group formed of random mutagenesis methods and directed mutagenesis methods.

There is performed a treatment by random mutagenesis in which bacteria corresponding to the strain deposited with the CNCM are subjected to at least one mutagenic agent chosen from the group formed of physical mutagenic agents—especially by exposing bacteria corresponding to the strain deposited with the CNCM to ultraviolet light radiation or to ionising radiation—and chemical mutagenic agents.

Mutant bacteria have differences in DNA sequence as compared with the bacteria of the strain deposited with the CNCM. These differences in DNA sequence affect DNA sequences different from the 16S rDNA sequence of the bacterium according to the invention.

According to one of the first or second advantageous variants of a method according to the invention, the treatment composition comprising bacteria having a DNA sequence that is 100% homologous with SEQ ID_NO1 (that is to say bacteria corresponding to the strain deposited with the CNCM and/or mutant bacteria of that deposited strain) is brought into contact with at least part of said plant material.

According to the first or second variants of a method according to the invention, the bacteria of the treatment composition can be bacteria in the vegetative growth phase. "Bacteria in the vegetative growth phase" are understood as being bacteria which have an active metabolism and/or which are multiplying by cell division. They are, therefore, living bacteria in the vegetative growth phase or in the stationary phase. The treatment composition is then formed of bacteria and of a culture medium. The culture medium is advantageously an aqueous culture medium. Advantageously, the aqueous culture medium is a culture medium chosen from the group formed of rich media comprising all the mineral elements and organic precursors necessary for the growth of the bacteria according to the invention, in particular a carbon source, a nitrogen source, a phosphorus source, vitamins and trace elements.

Advantageously, the aqueous culture medium can comprise D-glucose, a yeast extract, dibasic potassium phosphate, ammonium sulfate, potassium chloride and glycerol.

According to the first or second variants of a method according to the invention, the bacteria of the treatment composition can also be in the form of spores having the DNA sequence that is 100% homologous with sequence SEQ ID_NO1. The formation of spores is observed when the bacteria in the vegetative growth phase form a primary mycelium which develops at an air/solid interface and initiate aerial growth. Unbranched aerial filaments or "hyphae" develop from the primary mycelium and have at their ends compartmentalised structures which are precursors of spores. They can be spores of bacteria corresponding to the strain deposited and registered on 7 Apr. 2011 under number I-4467 with the National Collection of Microorganisms Cultures (CNCM) of the Pasteur Institute or of mutant bacteria of that deposited strain comprising a DNA sequence having the sequence SEQ ID_NO1. They are, therefore, living bacteria in the form of spores.

The spores of bacteria of the strain deposited with the CNCM are smooth spores linked together in "S"-type spirals, the smooth spore chains having on average from 10 to 50 spores.

The production of spores of the bacterium according to the invention is facilitated by culturing bacteria according to the invention in a culture medium which is liable to generate bacterial stress, especially a liquid culture medium which has a limited content of or is deficient in carbon and/or nitrogen and/or phosphorus and/or vitamins and/or trace elements.

Advantageously, such spores can be placed in a rich rehydration medium to form a population of bacteria according to the invention in the vegetative phase.

Advantageously, there is applied to the plant material a treatment composition comprising bacteria in the vegetative phase and/or bacteria in the form of spores. In any case, the vegetative forms and the spores of the bacteria have a 16S rDNA sequence that is 100% homologous with sequence SEQ ID_NO1.

The aqueous culture medium can be a solid aqueous culture medium or a liquid aqueous culture medium.

In a first embodiment of the first variant of a method according to the invention, the treatment composition comprising bacteria (deposited strain and/or mutant bacteria of the deposited strain) having the 16S rDNA sequence corresponding to SEQ ID_NO1 is a liquid treatment composition. Advantageously, the liquid treatment composition is an aqueous liquid treatment composition. The aqueous liquid treatment composition can therefore be formed of a bacterial load comprising bacteria having the 16S rDNA sequence corresponding to SEQ ID_NO1 in an aqueous liquid medium.

In the first embodiment, advantageously, there is applied to at least part of said plant material the liquid treatment composition comprising bacteria of the strain deposited with the CNCM and/or mutant bacteria in a liquid culture medium.

In a second embodiment of the first variant of a method according to the invention, the treatment composition comprising bacteria having the sequence SEQ ID_NO1 is a solid treatment composition.

In this second embodiment, advantageously, there is applied to at least part of said plant material the solid treatment composition comprising bacteria of the strain deposited with the CNCM and/or mutant bacteria and a solid culture medium. In this second embodiment, the solid culture medium can comprise a proportion of agar-agar (E406).

In a third variant of a method according to the invention, there is applied a treatment composition comprising at least one polynucleotide having at least one DNA sequence portion that is homologous with SEQ ID_NO1.

Advantageously, in the third variant of a method according to the invention, the treatment composition can comprise such a polynucleotide and/or bacteria chosen from the group formed of bacteria corresponding to the strain deposited and registered on 7 Apr. 2011 under number I-4467 with the National Collection of Microorganisms Cultures (CNCM) of the Pasteur Institute and/or mutant bacteria of that deposited strain.

Advantageously, in the third variant of a method according to the invention, the treatment composition can be an acellular composition, that is to say substantially free of bacteria having the sequence SEQ ID_NO1. In the third variant of a method according to the invention, at least part of said plant material is brought into contact with the acellular composition freed of bacteria having the sequence SEQ ID_NO1.

Advantageously and according to the invention, such an acellular composition is in particular a culture medium in which bacteria comprising the sequence SEQ ID_NO1 have developed and which is substantially free of said bacteria.

The invention relates also to a treatment composition formed of a bacterial culture medium which has an HPLC chromatogram comprising a first major signal ($P_{72,6}$) at a retention time of 11.925 min and a second major signal ($P_{72,14}$) at a retention time of 20.04 min.

Such a treatment composition formed of a bacterial culture medium according to the invention has an effect stimulating the growth of plants in cultivation, such as sunflower, maize, rape, wheat and tomato, and also has an antifungal activity—especially against *Botrytis cinerea*—on vine leaves.

Such a treatment composition can be a culture medium in which bacteria comprising the sequence SEQ ID_NO1 have developed and which is or is not substantially free of said bacteria.

An acellular composition according to the invention obtained after culturing the strain according to the invention for 24 hours can exhibit, when analysed by HPLC on a reverse phase column, a plurality of peaks ($P_{24,i}$) having retention times ($t_i$) listed in Table 1 below.

TABLE 1

| $P_{24,i}$ | $t_i$ (minute) |
| --- | --- |
| $P_{24,1}$ | 3.30-3.60 |
| $P_{24,2}$ | 3.90-4.0 |
| $P_{24,3}$ | 5.90-6.38 |
| $P_{24,4}$ | 10.1-10.20 |
| $P_{24,5}$ | 13.5-13.9 |
| $P_{24,6}$ | 21.4-21.7 |

Such an acellular composition according to the invention obtained after culturing the strain according to the invention for 3 days (72 hours) can exhibit, when analysed by HPLC on a reverse phase column, a plurality of peaks ($P_{72,i}$) having retention times ($t_i$) and areas ($A_{72,i}$), expressed in relative values under said peaks ($P_{72,i}$), listed in Table 2 below.

TABLE 2

| $P_{72,i}$ | $t_i$ (minute) | $A_{72,i}$ (%) |
| --- | --- | --- |
| $P_{72,1}$ | 3.93 | 3.45 |
| $P_{72,2}$ | 5.30 | 2.02 |
| $P_{72,3}$ | 6.59 | 5.05 |
| $P_{72,4}$ | 8.83 | 1.45 |
| $P_{72,5}$ | 9.63 | 3.13 |
| $P_{72,6}$ | 11.925 | 9.07 |

TABLE 2-continued

| $P_{72,i}$ | $t_i$ (minute) | $A_{72,i}$ (%) |
| --- | --- | --- |
| $P_{72,7}$ | 12.39 | 1.92 |
| $P_{72,8}$ | 12.87 | 1.24 |
| $P_{72,9}$ | 13.76 | 1.82 |
| $P_{72,10}$ | 15.93 | 2.68 |
| $P_{72,11}$ | 16.27 | 2.07 |
| $P_{72,12}$ | 18.41 | 1.98 |
| $P_{72,13}$ | 19.38 | 3.15 |
| $P_{72,14}$ | 20.04 | 6.59 |

There is analysed by HPLC the extract obtained by extracting the culture medium of the strain according to the invention with ethyl acetate, drying the ethyl acetate solution and dissolving the extract in methanol. HPLC chromatography is carried out on an Xbridge column (Waters, Guyancourt, France) of dimensions 25 cm/4.6 mm/5 µm. Elution is carried out by an acetonitrile gradient from 20% to 95% in water with a flow rate of 0.8 ml/min. Detection is carried out at a wavelength of 254 nm.

Under the extraction and analysis conditions mentioned above, advantageously and according to the invention, the treatment composition is an acellular composition which is substantially free of bacteria having the sequence SEQ ID_NO1 and is formed of a culture medium in which bacteria comprising said sequence SEQ ID_NO1 have developed and which is substantially free of said bacteria and which has an HPLC chromatogram comprising a first major signal ($P_{72,6}$) at a retention time of 11.925 min and a second major signal ($P_{72,14}$) at a retention time of 20.04 min.

Under the analysis conditions mentioned above, advantageously and according to the invention, the acellular composition obtained after culturing the strain according to the invention for 3 days (72 hours) has an HPLC chromatogram comprising signals, named minor signals, at retention times of 3.93 min, 5.30 min, 6.59 min, 8.83 min, 9.63 min, 12.39 min, 12.87 min, 13.76 min, 13.76 min, 15.93 min, 16.27 min, 18.41 min and 19.38 min.

Such an acellular composition is obtainable by a method wherein:
  at least one bacterium of the strain deposited with the CNCM and having the DNA sequence SEQ ID_NO1 is cultured in a culture medium capable of allowing said bacteria to grow, for a period greater than 24 hours; and then
  the bacteria are removed from the culture medium so as to form the acellular composition which is at least substantially free of said bacteria.

Advantageously, the bacteria are seeded and cultured in the culture medium for a period of time sufficient to allow them to grow, that is to say for a period of from a minimum period of approximately 24 hours to 10 days, at a temperature of from 12° C. to 37° C., preferably from 28° C. to 30° C., in particular of approximately 30° C., and then the bacteria are extracted from the culture medium—for example by centrifugation of the culture medium—or the bacteria are inactivated so as to form the acellular composition. Such an acellular composition is, therefore, a culture medium which no longer comprises the bacteria or which comprises dead bacteria, which has been obtained by contacting and culturing bacteria in a culture medium and under conditions which are suitable for the growth of said bacteria.

It is possible to inactivate the bacteria by any known technique, especially by lysis of the bacteria by enzymatic treatment or by mechanochemical treatment.

Advantageously and according to the invention, the treatment composition is applied to the part(s) of the plant material, said treatment composition further comprising at least one excipient which is acceptable (phyto-acceptable) to said plant material.

Advantageously and according to the invention, the plant material is chosen from the group formed of all or part of a plant in cultivation, of a fruit or vegetable after harvesting, and of seeds and propagating material—especially seeds, bulbs, tuberous roots, rhizomes or tubers—of plants. In particular, the treatment composition is applied to at least an aerial part of the plant, for example to the foliage or to the seeds.

Advantageously and according to the invention, the plant in cultivation is chosen from the group formed of fruit trees—especially olive trees, apricot trees, cherry trees, quince trees, almond trees, fig trees, hazel trees, walnut trees, peach trees, pear trees, apple trees, plum trees, vines and citrus fruits—, ornamental trees and shrubs, vegetable plants—especially asparagus, aubergines, Swiss chard, beetroot, carrot, celery, chicory, endives, cruciferous plants or brassicas (for example cabbages), cucumbers, gherkins, courgettes, shallots, onions, field beans, spring beans, winter beans, strawberry plants, raspberry plants, beans, lettuce, curly endives, broad-leaved endives, hops, lentils, alfalfa, lamb's lettuce, maize, melons, turnips, leeks, peas, peppers, potatoes, radishes, swede, soya, tobacco, tomatoes, sunflowers—, cereals—especially wheat, rape, flax, seed flax, fibre flax, barley, sorghum—, various floral crops—especially chrysanthemums, hydrangeas, carnations, roses, tulips—, and aromatic plants—especially parsley, garlic, chives.

Advantageously and according to the invention, the plant material is chosen from the group formed of plant seeds, aerial parts of plants and roots of plants.

Advantageously, the treatment composition is applied to plant seeds in order to activate the germination thereof.

Advantageously, the treatment composition is applied to the aerial parts of plants for phytosanitary treatment of the plants or for a treatment stimulating the natural defences of the plants or for a treatment stimulating the growth of the plants.

Accordingly, the invention relates to a method for treating plant material, wherein there is applied to at least part of said plant material a treatment composition comprising at least one biological material chosen from the group formed of:
- at least one bacterium comprising a DNA sequence that is 100% homologous with SEQ ID_NO1;
- a liquid composition comprising a DNA sequence that is 100% homologous with SEQ ID_NO1;
- a solid composition comprising a DNA sequence that is 100% homologous with SEQ ID_NO1;
- an acellular composition comprising a DNA sequence that is 100% homologous with SEQ ID_NO1.

Nutrition

Advantageously and according to the invention, there is used a treatment composition comprising a solid nutriment in the divided state. The treatment composition further comprising at least one solid nutriment in the divided state is therefore applied to all or part of the plant in cultivation. The treatment composition comprising at least one nutriment in the solid state and at least one biological agent comprising a DNA sequence that is more than 99%—limit excluded—homologous with SEQ ID_NO1. In particular, advantageously and according to the invention, said treatment composition is applied to the cultivation substrate—especially to the soil—of the plant. However, it is also possible to apply the treatment composition to the aerial parts of the plants. The inventors have observed that a treatment composition comprising bacteria comprising a DNA sequence that is more than 99%—limit excluded—homologous with SEQ ID_NO1—especially bacteria of the strain as deposited with the CNCM—allows the solubilisation of solid nutriments—especially of phosphorus—of a plant cultivation substrate to be improved, thus promoting the nutrition and fertilisation of the plants.

Stimulation of the Growth of Plants

Advantageously and according to the invention, said treatment composition is applied to said plant material in order to activate the growth thereof.

In particular, advantageously and according to the invention, said treatment composition is applied to seeds so as to activate the germination of the seeds. The inventors have observed that the application of a treatment composition according to the invention comprising bacteria in the vegetative state and/or in the form of spores to seeds—especially to sunflower seeds or to maize seeds—allows the germination of the seeds and the growth of the sunflower and maize plants to be accelerated.

Inhibition of Phytopathogens

Advantageously and according to the invention, said treatment composition is applied to said plant material in order to inhibit the growth of at least one target microorganism. Said treatment composition is applied to said plant material in order to inhibit the growth of target microorganisms chosen from the group formed of phytopathogenic microorganisms (bacteria or fungi). In particular, advantageously and according to the invention, said treatment composition is applied to at least a foliage part of plants. It is possible for the treatment composition to be a curative treatment composition or a prophylactic (or preventive) treatment composition for said plant material. Consequently, the treatment composition is applied prior to the appearance of the disease or after the appearance of the disease.

Stimulation of the Natural Defences of the Plants

Advantageously and according to the invention, said treatment composition is applied to said plant material in order to stimulate the natural defences of said plant material.

The inventors have observed, unforeseeably and unexpectedly, that a treatment composition according to the invention allows the self-defence mechanisms of plants to be stimulated—especially allows the ionic fluxes and/or the expression of the PR-1 (pathogenesis-related protein of type 1) gene—which is responsible for the synthesis of defence compounds in the plant—to be activated.

The invention extends to a treatment composition for plant material comprising at least one biological agent chosen from the group formed of:
- bacteria comprising a DNA sequence, named 16S rDNA, which codes for the 16S ribosomal RNA of said bacterium and is 100% homologous with SEQ ID_NO1,
- culture media in which bacteria comprising the 16S rDNA sequence that is 100% homologous with SEQ ID_NO1 have developed and which are substantially free of said bacteria, said culture media comprising polynucleotides having a DNA sequence that is 100% homologous with SEQ ID_NO1, and wherein the bacteria are chosen from the group formed of bacteria corresponding to the strain deposited and registered on 7 Apr. 2011 under number I-4467 with the National Collection of Microorganisms Cultures (CNCM) of the Pasteur Institute, and mutant bacteria of that deposited strain.

The invention extends to such a treatment composition for plant material.

The inventors have observed that such a treatment composition according to the invention:
- is capable of slowing the growth of certain bacteria such as *Micrococcus luteus* and *Bacillus subtilis*;
- is capable of slowing the growth of certain phytopathogenic target microorganisms such as *Botrytis cinerea*, *Streptomyces scabies*, *Botrytis cinerea*, *Fusarium culmorum*, *Pythium ultimum*, *Phaeomoniella chlamydospora*, *Phaeomoniella aelophilum*, *Eutypa lata*, *Fomitiporia mediterranea* and *Botryosphaeria obtusa*; and
- has an effect stimulating the growth of plants in cultivation, such as sunflower and maize; and
- is capable of stimulating the natural defences of plants in cultivation.

In particular, the inventors have found that a treatment composition according to the invention has an activity stimulating the natural defences of plants, that is to say are capable of activating the expression in the plants of defence genes—for example PR-1—against pathogenic organisms of plants.

Advantageously and according to the invention, the treatment composition is liquid. In particular, the treatment composition is liquid at ambient temperature.

Advantageously and according to the invention, the treatment composition is solid. In particular, the treatment composition is solid at ambient temperature.

Advantageously and according to the invention, the treatment composition comprises at least one acceptable (phytoacceptable) excipient for permitting its application to a plant material to be treated.

The invention relates also to any agricultural use of a treatment composition according to the invention, that is to say of a treatment composition comprising at least one biological agent chosen from the group formed of:
- bacteria comprising a DNA sequence, named 16S rDNA, which codes for the 16S ribosomal RNA of said bacterium and is 100% homologous with SEQ ID_NO1,
- polynucleotides having a DNA sequence that is 100% homologous with SEQ ID_NO1, and wherein the bacteria are chosen from the group formed of bacteria corresponding to the strain deposited and registered on 7 Apr. 2011 under number I-4467 with the National Collection of Microorganisms Cultures (CNCM) of the Pasteur Institute, and mutant bacteria of that deposited strain.

In particular, the invention relates to any agricultural use of a treatment composition according to the invention comprising at least one bacterium of the strain as deposited with the CNCM and having the DNA sequence SEQ ID_NO1.

More particularly, the invention relates to the use of such a treatment composition for:
- stimulating the growth of plants; or
- stimulating the germination of seeds; or
- fertilisation treatment of plants; or
- antimicrobial treatment—especially antifungal treatment or antibacterial treatment—and/or antiviral treatment of plants; or
- stimulating the natural defences of plants.

The invention relates also to a method for treating plant material, to a treatment composition for plant material and to the agricultural use of such treatment compositions, characterised in combination by all or some of the features mentioned hereinabove or hereinbelow.

BRIEF DESCRIPTION OF THE DRAWINGS

Other objects, features and advantages of the invention will become apparent from reading the following description, the illustrative examples, which are given without implying any limitation, and the accompanying figures, in which:

FIG. 2 is a reproduction of a photograph showing the inhibition of the growth of a pathogenic fungus by the bacteria according to the invention;

FIG. 3 is a reproduction of a photograph illustrating the solubilisation of calcium phosphate by bacteria according to the invention;

FIG. 7 is a photograph of an electrophoresis gel showing the stimulation of the expression of the PR-1 natural defence protein of plants by a composition according to the invention;

Figure 1A:
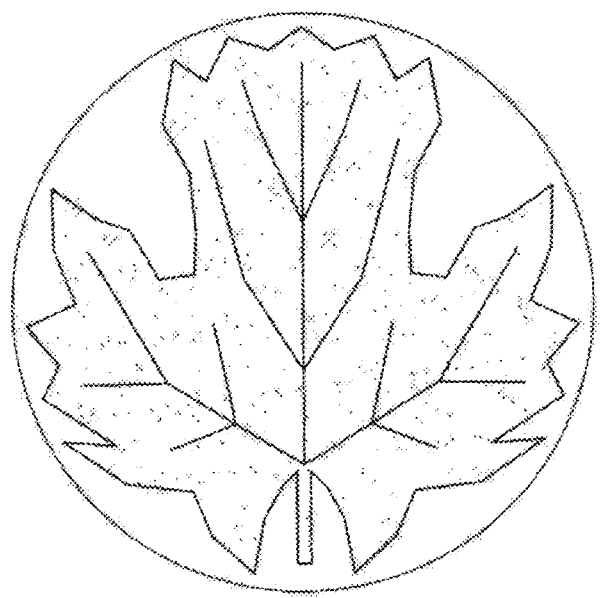
FIG. 1 is a reproduction of comparative photographs (1a and 1b) of vine leaves showing the protective/curative effect with regard to *Botrytis cinerea* of a treatment with a treatment composition according to the invention.

The strain of *Streptomyces* deposited with the CNCM under no. I-4467 was isolated from a sample of the rhizosphere and the deep roots of a vine stock. The sample of the rhizosphere was taken at a depth of from 10 cm to 50 cm beneath the surface of the soil, the superficial portion of the sample being removed, and was placed in a sterile, hermetically sealed sachet and stored at +4° C. prior to isolation of the *Streptomyces* strains.

The sample is suspended in distilled and sterile water at a rate of 4 g of sample in 36 ml of water, with magnetic stirring at a speed of 200 revolutions per minute for 30 minutes. The suspension obtained is then placed at a temperature of 50° C. for 10 minutes. The suspension is then diluted in sterile distilled water according to a dilution factor of $10^{-7}$. 0.1 ml of the dilution is spread in sterile manner over a Petri dish containing a solid agar culture medium SEA (soil extract agar) supplemented with nalidixic acid (10 mg/l) or novobiocin (25 mg/l) as antibiotics and/or with cycloheximide (40 mg/l) as an antifungal. The Petri dishes are then placed in an incubator at a temperature of 30° C. for 21 days.

The actinomycetes bacteria are isolated by spreading, observation under an optical microscope and visual recognition of their morphological characteristics. The actinomycetes bacteria so isolated and purified are transferred to Bennett's medium for cloning. The isolated colonies are maintained at 4° C. for two months, removed and suspended in 20% sterile glycerol before being placed and stored at −20° C.

In order to analyse the 16S rDNA sequence of the bacterium to be identified, said bacteria are cultivated in a liquid medium, and their genomic DNA is then extracted and the 16S rDNA sequence is selectively amplified—especially by PCR (polymerase chain reaction)—by PCR using:
  a universal primer "27f" of the following sequence SEQ ID_NO2: "agagtttgat cctggctcag"; and
  a universal primer "1492r" of the following sequence SEQ ID_NO3:
  "ggttaccttg ttacgactt". Sequencing of the 16S rDNA is then carried out by any method known to the person skilled in the art, and the 16S rDNA sequence obtained is compared with sequence SEQ ID_NO1.

To that end, the bacteria to be identified are cultivated, with stirring, in 100 ml of liquid ISP-2 medium (ISP Medium 2, International *Streptomyces* Project Yeast Malt Extract Agar) at 30° C. for 5 days. The mycelium obtained and the culture medium are separated by centrifugation, and the mycelium is washed twice with double-distilled water. Lysis of the mycelium is carried out in 500 µl of lysis buffer (Tris-HCl 400 mM, EDTA 60 mM, NaCl 150 mM, SDS 1%, pH 8.0) for 10 minutes at ambient temperature. 150 µl of a solution (pH 4.8) obtained by mixing 60 ml of 5M potassium acetate, 11.5 ml of glacial acetic acid and 28.5 of distilled water are then added to the lysis medium, and vigorous stirring is carried out. The lysis medium obtained is centrifuged at 10,000 g for 1 minute. The supernatant is collected and subjected to a further centrifugation step at 10,000 g for 1 minute. The supernatant is collected, and an equal volume of isopropanol is added thereto. After stirring, centrifugation is carried out at 10,000 g for 2 minutes. The precipitated DNA is washed with 300 µl of 70% ethyl alcohol, centrifuged and then dried in the air and dissolved in 50 µl of sterile double-distilled water.

The PCR is carried out using a kit (InVitrogen) and according to a thermal profile (Techne Touch Gene PCR Thermal Cycler):
  denaturing at 98° C. for 3 min;
  addition of "Taq-polymerase";
  30 amplification cycles comprising:
    a phase of heating at 94° C. for 1 min, followed by
    a phase of heating at 52° C. for 1 min, followed by
    a phase of heating at 72° C. for 2 min, followed by;
  extension step at 72° C. for 10 min.

The PCR product is analysed and detected on electrophoresis gel and revealed by ethidium bromide under ultraviolet light. The 16S rDNA sequence of the bacteria to be identified is then compared with sequence SEQ ID_NO1.

In a first embodiment of a first variant of a method for treating plant material according to the invention, a treatment composition comprising at least one bacterium in vegetative form and having a DNA sequence that is more than 99%—limit excluded—homologous with SEQ ID_NO1 is prepared by seeding a culture medium, for example a liquid culture medium or a solid culture medium, with an inoculum of bacteria of the strain deposited with the CNCM under no. I-4467 or of at least one mutant thereof having the DNA sequence SEQ ID_NO1. The culture medium can be a complete (or empirical) medium, that is to say an undefined rich medium comprising all the elements necessary for the growth of the bacteria of the strain deposited with the CNCM. One volume of an inoculum of the bacterium deposited with the CNCM is seeded in twenty volumes of complete medium. The culture is kept at a temperature of 30° C., with stirring, for 5 days.

Such a complete medium for the production of a treatment composition comprising bacteria in vegetative form comprises, for example, D-glucose, a yeast extract, dibasic potassium phosphate ($K_2HPO_4$), ammonium sulfate (($NH_4$)$_2SO_4$), potassium chloride (KCl) and glycerol at pH 7.2.

In a second embodiment of a first variant of a method for treating plant material according to the invention, a treatment composition comprising at least one bacterium in the form of spores and having a DNA sequence that is 100% homologous with SEQ ID_NO1 is prepared by seeding a sporulation medium with an inoculum of the bacterium deposited with the CNCM under no. I-4467 or a mutant thereof. The sporulation medium can be, for example, a medium comprising D-glucose, a yeast extract, a peptone, calcium carbonate ($CaCO_3$) and distilled water at pH 7.2. The culture is kept at a temperature of 30° C. for 6 days.

In a second variant of a method for treating plant material according to the invention, an acellular composition is prepared by centrifuging a culture medium according to the first embodiment or a sporulation medium according to the second embodiment from which the bacteria and/or the spores have substantially been eliminated.

Example 1—Fertilisation

The bacteria according to the invention corresponding to the strain as deposited with the CNCM promote the solubilisation of solid nutritional elements—especially phosphorus—in a culture medium. The inventors have observed (FIG. 3), in a solid agar culture medium 9 opacified by a calcium phosphate powder, the formation of a translucent halo 10 surrounding the colonies 2 of bacteria according to the invention, demonstrating that the calcium phosphate has been solubilised by the bacteria. The bacteria according to the invention allow the dissolution—in the rhizosphere of plants—of a solid fertilisation product which cannot be assimilated by said plants to be increased and the nutrition of plants to be improved.

Example 2—Stimulation of the Growth of Sunflower and Maize

Figure 4:
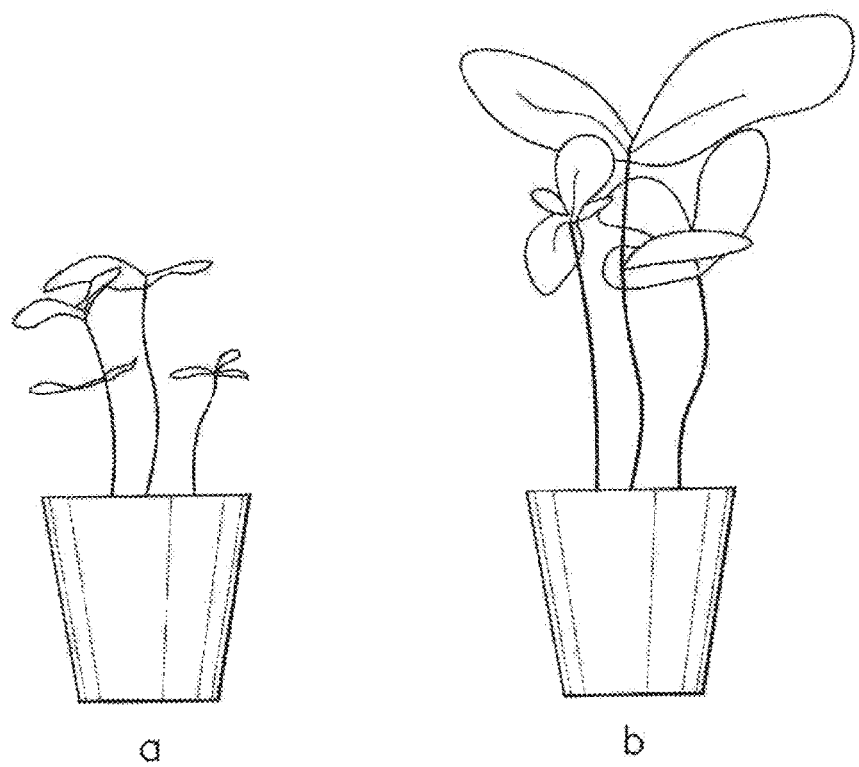
FIG. 4 is a reproduction of a photograph illustrating the stimulation of the growth of a sunflower plant by treatment of the sunflower seeds with a liquid composition according to the invention.
Figure 5:
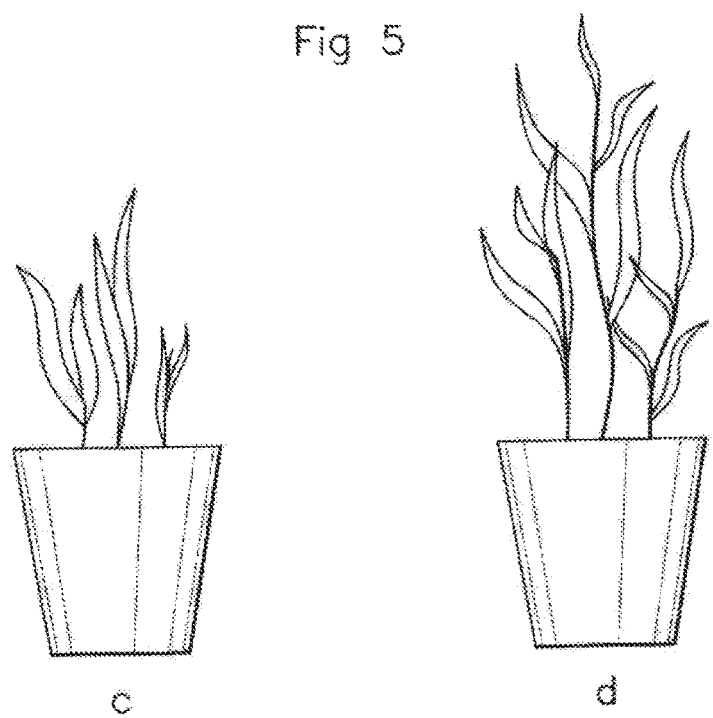
FIG. 5 is a reproduction of a photograph illustrating the stimulation of the growth of a maize plant by treatment of the maize seeds with a liquid composition according to the invention.
Figure 6A:
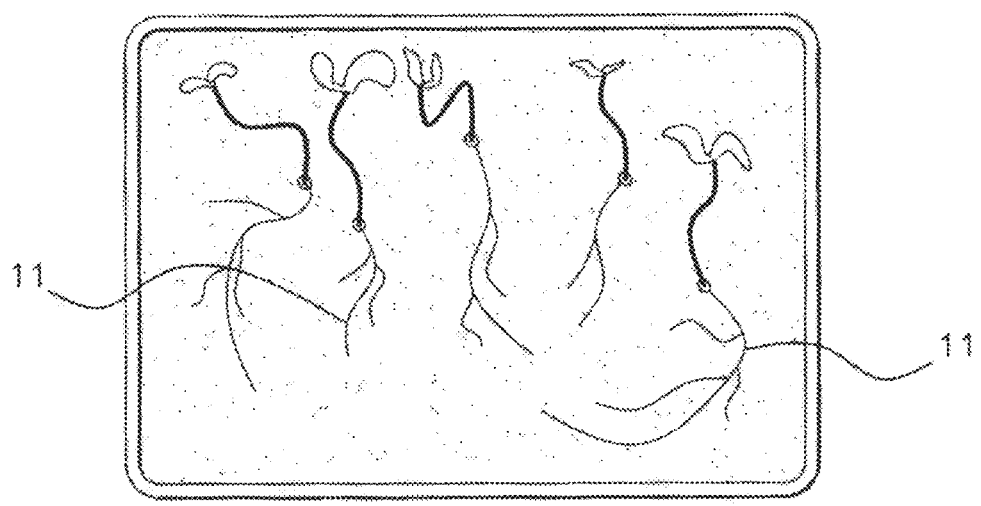
FIGS. 6a and 6b are reproductions of photographs illustrating the stimulation of the root growth of rape plantlets by a liquid composition comprising bacteria according to the invention.
Figure 6B:
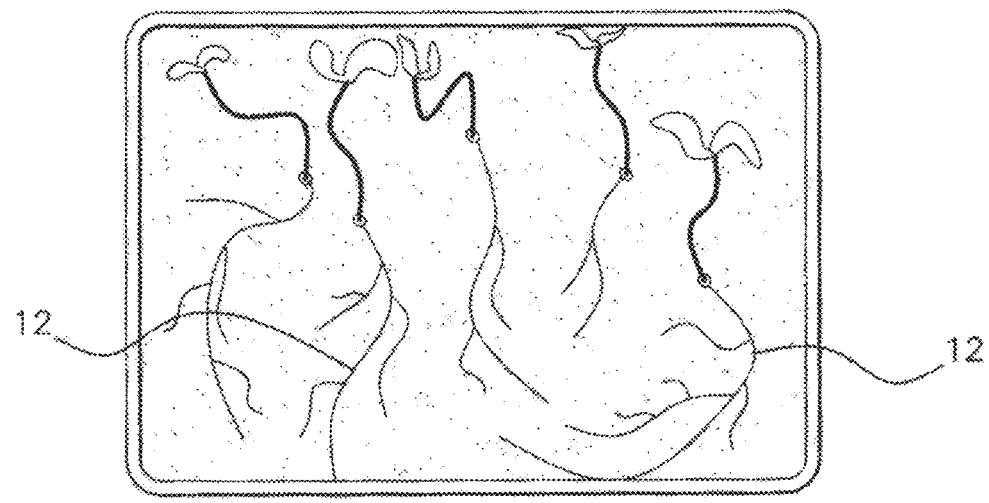

A liquid composition according to the invention comprising vegetative cells and spores of the bacterium according to the invention is prepared and is applied to sunflower seeds and to maize seeds by film coating. The liquid composition comprises from 1 to 2 g of bacteria per liter of composition, the mass of bacteria being the mass of the wet bacteria. There are carried out in parallel the sowing of seeds and the cultivation of plants of sunflower (FIG. 4a) and of maize (FIG. 5c) as controls which have not been treated with a composition according to the invention. The inventors have also observed a stimulation of the initial growth of the sunflower plants (FIG. 4b) and of maize plants (FIG. 5d). The bacteria according to the invention, when applied to the seeds, allow the growth of plants—in particular the growth of the aerial parts of plants—such as sunflower and maize to be stimulated.

Example 3—Protection of Vine Leaves from *Botrytis cinerea*

Figure 1B:
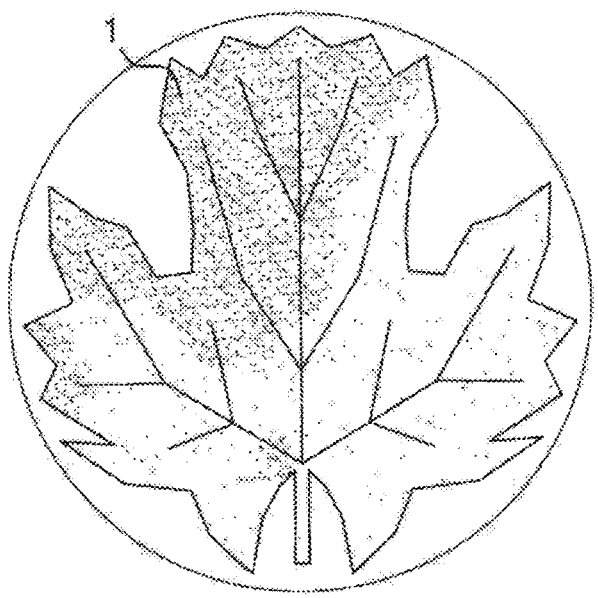

The application of spores of the strain according to the invention deposited with the CNCM to vine leaves allows the appearance of the symptoms (brown spots on the leaves, shown by a greyed pattern 1 in FIG. 1b) caused by the fungus *Botrytis cinerea* to be prevented/eliminated on the pretreated vine leaves. FIG. 1 shows a reproduction of a photograph of vine leaves pretreated (FIG. 1a) or not pretreated (FIG. 1b) with a composition of spores of the bacterium according to the invention and infected by *Botrytis cinerea*. Such an application also allows the germination of the spores of the fungus *Botrytis cinerea* applied subsequently to those vine leaves and the development thereof to be inhibited.

Example 4—Inhibition of the Growth of a Target Microorganism

The inhibitory activity on the growth of a target microorganism is determined and quantified using the cylinder method (Bauer et al., 1996), in which the bacteria of the strain deposited with the CNCM are seeded on solid Bennett's agar medium and the seeded medium is placed at 30° C. for 5 days so as to form a solid treatment composition. A cylindrical fragment, for example a cylindrical fragment having a diameter of 6 mm, of the solid treatment composition is removed, and the cylindrical fragment is deposited on the surface of a culture medium seeded with a target microorganism, for example a phytopathogenic target microorganism. The culture medium of the target microorganism can be, for example, a PDA (potato dextrose agar) medium for phytopathogenic fungi or Bennett's medium for phytopathogenic bacteria. The cylindrical fragment is kept on the surface of the culture medium seeded with the target microorganism for 4 hours at a temperature of 4° C. so as to allow compounds to diffuse from the culture medium of the bacterium according to the invention into the medium seeded with the target microorganism.

The medium seeded with the target microorganism is placed at 30° C. for 48 hours. The diameter of the zone of inhibition of the growth of the target microorganism is measured.

The solid treatment composition according to the invention exhibits an inhibitory activity on the growth of bacteria and/or phytopathogenic fungi. The spectrum of activity of the solid treatment composition with regard to the growth of microorganisms is shown in Table 3 below, in which the symbol (−) corresponds to the absence of inhibitory activity, the symbol (+) corresponds to an inhibition zone diameter of from 10 mm to 15 mm, the symbol (++) corresponds to an inhibition zone diameter of from 15 mm to 20 mm, and the symbol (+++) corresponds to an inhibition zone diameter greater than 20 mm.

TABLE 3

| Target microorganism | Inhibitory activity |
|---|---|
| *Phaeomoniella chlamydospora* | +++ |
| *Phaeomoniella aelophilum* | +++ |
| *Fomitiporia mediterranea* | ++ |
| *Eutypa lata* | +++ |
| *Botryosphaeria obtusa* | ++ |
| *Botryosphaeria dothidea* | ++ |
| *Botrytis cinerea* | ++ |
| *Verticillium dahliae* | +++ |
| *Fusarium culmorum* | +++ |
| *Pythium ultimum* | ++ |
| *Micrococcus luteus* | +++ |
| *Bacillus subtilis* | +++ |
| *Pseudomonas fluorescens* | − |

Under these conditions, the diameter of the zone of inhibition of the growth of the mycelium of the strain *Botrytis cinerea* by the strain according to the invention is 28 mm, the diameter of the zone of inhibition of the growth of the mycelium of the strain *Fusarium culmorum* is 30 mm, and the diameter of the zone of inhibition of the growth of the mycelium of the strain *Pythium ultimum* is 26 mm. The bacteria according to the invention advantageously have the ability to inhibit the growth of phytopathogenic agents of vines, such as, for example, *Phaeomoniella chlamydospora*, *Phaeomoniella aelophilum*, *Eutypa lata*, *Fomitiporia mediterranea* and *Botryosphaeria obtusa*.

The solid treatment composition comprising bacteria of the strain deposited with the CNCM allows the development of bacterial or fungal phytopathogenic agents to be limited.

FIG. 2 shows the large distance inhibition of the growth of the mycelium 8 of the fungus *Phaeomoniella chlamydospora*, chosen as a pathogenic agent of vine wood, by the bacteria 2 of the strain according to the invention deposited with the CNCM as compared with the inhibition of the growth of the mycelium 8 of the fungus *Phaeomoniella chlamydospora* by collection strains 3, 4 and 5 different from the strain according to the invention. It is to be noted that collection strains 7 and 8 do not inhibit the growth of the mycelium 8 of the pathogenic agent. The bacteria according to the invention allow the development of bacterial or fungal phytopathogenic agents to be limited.

Example 5—Stimulation of the Natural Defences (SND) of *Arabidopsis thaliana*

Bacteria of the genus *Streptomyces* of the strain deposited with the CNCM under no. I-4467 are cultured in a deficient liquid culture medium suitable for promoting the production of spores, for a period of time sufficient to allow said strain to grow. A pre-culture in the stationary growth phase comprising from 1 to 2 g of bacteria per liter of pre-culture is obtained, the mass of bacteria being the mass of the wet bacteria. A treatment composition according to the invention is then formed by diluting one volume of the pre-culture in 100 volumes of water. The roots of *Arabidopsis thaliana* plantlets are brought into contact with the treatment composition comprising bacteria according to the invention, and said plantlets are then sown on Gamborg B5 agar culture medium previously seeded with a suspension of *Botrytis cinerea* spores as the phytopathogenic agent (at a concentration of $10^5$ colony forming units (cfu)). The seeded culture medium is placed in a chamber at 25° C.

After one week, it is noted that the preventive treatment according to the invention of the *Arabidopsis thaliana* plantlets with the treatment composition comprising bacteria according to the invention allows the effect of *Botrytis cinerea* to be prevented by preventing the germination thereof (systemic effect) and by stimulating the natural defences of the *Arabidopsis thaliana* plantlets against *Botrytis cinerea*. By way of control, *Arabidopsis thaliana* plantlets which have not been treated with the treatment composition according to the invention are cultured on Gamborg B5 nutritive agar culture medium which has previously been seeded with a suspension of *Botrytis cinerea* spores.

The expression of the defence genes of the *Arabidopsis thaliana* plantlets, and in particular the expression of the PR-1 (pathogenesis-related protein of type 1) gene, which is responsible for the synthesis of antifungal compounds in plants, is measured by RT-PCR. The activation of the genes of *Arabidopsis thaliana* plantlets is analysed after the *Arabidopsis thaliana* plantlets have been growing for ten days. To that end, the messenger RNAs (mRNA) of the plantlets (of the control and of the preventive treatment according to the invention) are extracted, and the mRNAs are converted into cDNA (complementary DNA) using the "SuperScript™" II RNAse H Reverse Transcriptase kit (InVitrogen, Carlsbad, USA) and an oligo(dT)22 primer.

The cDNAs specific to PR-1 are amplified by PCR by means of the following specific primers:

```
"PR-1 f" having the following sequence SEQ ID_NO 4:
5'-CTGGCTATTCTCGATTTTTAATCG-3';
and "PR-1 r" having the following sequence SEQ ID_NO 5:
5'-TCCTGCATATGATGCTCCTTATTG-3'.
```

There are further amplified, as expression control, the cDNAs specific to the EF-1αA4 gene (Liboz et al., (1990), *Plant Mol. Biol.*, 14, 107-110. *The four members of the gene family encoding the Arabidopsis thaliana translation elongation factor EF-1α are actively transcribed*) by PCR using the following specific primers:

```
"EF-1f" having the following sequence SEQ ID_NO 6:
5'-ATGCCCCAGGACATCGTGATTTCA-3';
and "EF-1r" having the following sequence SEQ ID_NO 7:
5'-TTGGCGGCACCCTTAGCTGGATCA-3'.
```

The PCR products are analysed by gel electrophoresis and visualised under ultraviolet light in the presence of ethidium bromide. The results are given in FIG. 7. A stimulation of the expression of the PR-1 gene is observed in the *Arabidopsis thaliana* plantlets treated with the treatment composition (A2) as compared with the control *Arabidopsis thaliana* plantlets which were not treated (A1) with the treatment composition, in which the expression of PR-1 is undetectable.

A stimulation of the expression (B) of the PAL 1 gene is observed in the *Arabidopsis thaliana* plantlets treated with the treatment composition (B4) as compared with the *Arabidopsis thaliana* plantlets not treated (B3) with the treatment composition, said PAL 1 gene being known to constitute a molecular marker and a positive control of stimulation of the natural defences of plants.

For the gene EF1αA4 (negative control of normalisation of the level of gene expression), substantially unchanged expression is observed in the *Arabidopsis thaliana* plantlets (C5) not treated with the bacterium of the genus *Streptomyces* and in the *Arabidopsis thaliana* plantlets (C6) treated with the bacterium of the genus *Streptomyces*.

Treatment of the *Arabidopsis thaliana* plantlets with the bacterium of the genus *Streptomyces* leads to activation of the PR-1 gene, to the production of plant antibiotics, and to the production of phytoalexins and of compounds which are to reinforce the walls of the plant cells.

Figure 8:
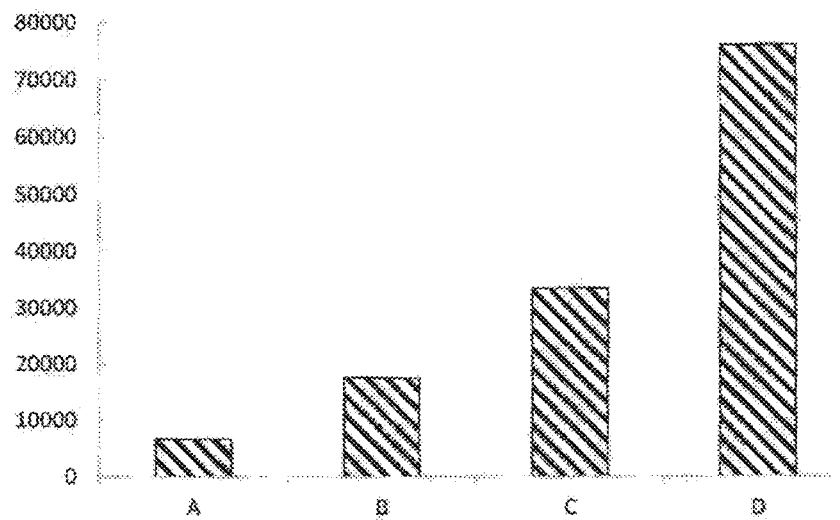
FIG. 8 is a representation in graph form of the effect of a composition according to the invention on the stimulation of the calcium flux.

Example 6—Stimulation of the Natural Defences (SND) of *Arabidopsis thaliana*—Stimulation of the Calcium Flux The calcium flux induced by treating *Arabidopsis thaliana* plantlets with a treatment composition obtained by diluting the pre-culture described in Example 5 by a factor of 10× or by a factor of 100× is measured by luminescence. The results are shown in FIG. 8. 20 minutes after treatment with the treatment composition (B) diluted 100×, an increase in the calcium flux by a factor of 2.7 relative to treatment with water (A) is observed. There is also observed, 20 minutes after treatment with the treatment composition (D) diluted 10×, an increase in the calcium flux by a factor of 11.6 relative to treatment with water (A) and by a factor of 2.3 relative to treatment with a positive control (C) of induction of the natural defences of plants and comprising a parietal extract of the pathogenic oomycetes *Phytospora parasitica*.

The treatment compositions diluted 10× or 100× according to the invention activate the early stages of the natural defences of plants.

Figure 9:
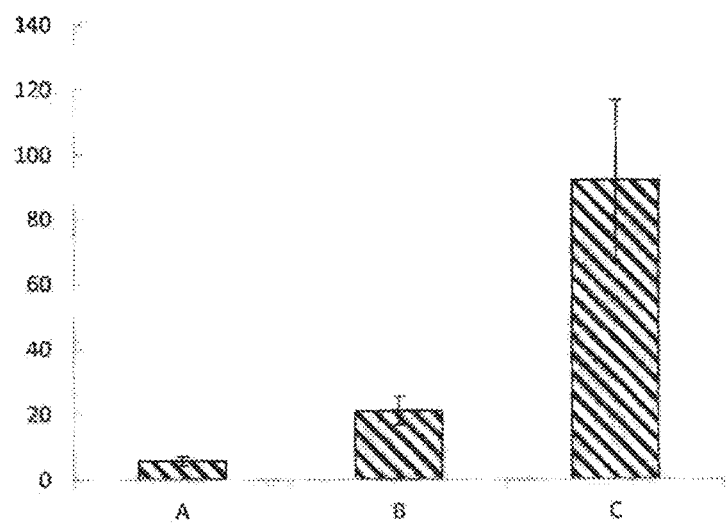
FIG. 9 is a representation in graph form of the effect of a composition according to the invention on the expression of the PR-1 gene of a plant.

Example 7—Expression of PR-1 48 Hours after Treatment with a Treatment Composition According to the Invention The level of expression of the PR-1 gene of *Arabidopsis thaliana* transgenic model is analysed by fluorimetry 48 hours after treatment with a treatment composition diluted 100× as described in Example 5. The results are given in FIG. 9. There is observed an increase in the level of expression of the PR-1 gene (expressed in fluorescence units per mg of protein) of the plant treated with the treatment composition according to the invention and diluted 100× (C) by a factor of 16 relative to the level of expression of the PR 1 gene in the plant treated with water (A) and by a factor of 4.4 relative to the level of expression of the PR 1 gene in the plant treated with a positive control (B) of induction of the natural defences of the plants and comprising a parietal extract of the pathogenic oomycetes *Phytospora parasitica*.

Example 8—Protection of *Arabidopsis thaliana* Plantlets Against *Colletotrichum higginsianum*

The protection conferred by an acellular composition according to the invention against infection by *Colletotrichum higginsianum* is evaluated on *Arabidopsis thaliana* plantlets by luminescence. An acellular composition according to the invention is prepared by diluting by a factor of 10× a pre-culture of bacteria according to the invention comprising 1 mg of biomass per ml of pre-culture. The acellular composition according to the invention is subjected to a thermisation treatment (15 min at 90° C.). The thermised acellular composition is applied to 3-week-old *Arabidopsis thaliana* plantlets for 48 hours and then the plantlets are inoculated with *Colletotrichum higginsianum*. Protection against *Colletotrichum higginsianum* that is improved (1600 rfu) as compared with a negative control (2000 rfu) is observed. The protection conferred by the thermised acellular composition is substantially equivalent to the protection conferred by the non-thermised acellular composition.

The invention can of course be the subject of many variant embodiments and applications.

SEQUENCE LISTING

SEQ ID_NO 1

```
tagtggcgaa cgggtgagta acacgtgggc aatctgccct gcactctggg acaagccctg    60
gaaacggggt ctaataccgg atatgacacg ctcccgcatg ggatgcgtgt ggaaagctcc   120
ggcggtgcag gatgagcccg cggcctatca gcttgttggt ggggtgatgg cctaccaagg   180
```

```
                             SEQUENCE LISTING cgacgacggg tagccggcct gagagggcga ccggccacac tgggactgag acacggccca    240
gactcctacg ggaggcagca gtggggaata ttgcacaatg ggcgaaagcc tgatgcagcg    300
acgccgcgtg agggatgacg gccttcgggt tgtaaacctc tttcagcagg gaagaagcga    360
gagtgacggt acctgcagaa gaagcgccgg ctaactacgt gccagcagcc gcggtaatac    420
gtagggcgca agcgttgtcc ggaattattg ggcgtaaaga gctcgtaggc ggcttgtcgc    480
gtcggatgtg aaagcccggg gcttaacccc gggtctgcat tcgatacggg caggctagag    540
ttcggtaggg gagatcggaa ttcctggtgt agcggtgaaa tgcgcagata tcaggaggaa    600
caccggtggc gaaggcggat ctctgggccg atactgacgc tgaggagcga aagcgtgggg    660
agcgaacagg attagatacc ctggtagtcc acgccgtaaa cgttgggaac taggtgtggg    720
cgacattcca cgtcgtccgc gccgcagcta acgcattaag ttccccgcct ggggagtacg    780
gccgcaaggc taaaactcaa aggaattgac ggggggcccg cacaagcggc ggagcatgtg    840
gcttaattcg acgcaacgcg aagaacctta ccaaggcttg acatacaccc ggaaacctct    900
ggagacaggg gccccccttg tggtcggtgt acaggtggtg catggcttgt cgtcagctcg    960
tgtcgtgaga tgttgggtta agtccccgca acgagcgcaa cccttgttct gtgttgccag   1020
catgcctttc gggggntgat ggggactttnc acaggagact gccggggtca actcggagga   1080
aggtggggac gacgtcaagt catcatgccc cttatgtctt gggctgcaca cgtgctacaa   1140
tggccggtac aatgagctgc gaagccgtga ggtggagcga atctcaaaaa gccggtctca   1200
gttcggattg ggtctgcaa ctcgacccca tgaagtcgga gtcgctagta atcgcagatc    1260
agcattgctg cggtgaatac gttcccgggc cttgtacaca ccgcccgtca cgtcacgaaa   1320
gtcggtaaca cctgaa                                                   1336

SEQ ID_NO 2
agagtttgat cctggctcag                                                 20

SEQ ID_NO 3
ggttaccttg ttacgactt                                                  19

SEQ ID_NO 4
ctggctattc tcgatttta atcg                                             24

SEQ ID_NO 5
tcctgcatat gatgctcctt attg                                            24

SEQ ID_NO 6
atgccccagg acatcgtgat ttca                                            24

SEQ ID_NO 7
ttggcggcac ccttagctgg atca                                            24

SEQ ID_NO 8
ttggccgcct cgcgcaacgc ctcgactgcc aatacgaaca atggcgccag caccgccccg     60
ctgcgcatct cctttgcgaa gatcagggag cctctcgagg ttccgaacct cctcgcgctg    120
cagaccgaga gcttcgattg gctgctcggc aatgccgcct ggaaggctcg cgtcgaggct    180
gcgctggaca gcggtcagga cgtccccacc aagtccggtc tggaagagat cttcgaggag    240
atctccccga tcgaggactt ctccgggtcg atgtccctga cttccgtga tcaccgtttc     300 gagccgccga agaactcgat cgacgagtgc aaggagcgtg acttcaccta cgccgctccg    360
ctcttcgtca cggccgagtt caccaacaac gagaccggcg agatcaagtc ccagacggtc    420
ttcatgggcg acttcccgct catgaccgac aagggcacct tctgcatcaa cggcaccgag    480
cgtgtcgtcg tctcgcagct ggtccgctcg ccgggtgtct acttcgactc ctccatcgac    540
```

```
                              SEQUENCE LISTING aagacgtccg acaaggacat cttctccgtc aaggtcatcc cgtcccgggg tgcctggctg    600
gagatggaga tcgacaagcg tgacatggtc ggtgtgcgta tcgaccgcaa gcgcaagcag    660
tccgtcaccg ttctcctgaa ggctctcggc tggacgaccg agcagatcct ggaggagttc    720
ggcgagtacg agtcgatgcg cgccaccctg gagaaggacc acacccaggg ccaggacgac    780
gcgctgctcg acatctaccg caagctgcgt ccgggcgagc cccccacacg ggaggccgcg    840
cagacgctgc tcgagaacct ctacttcaac ccgaagcgct acgacctcgc gaaggtcggc    900
cgctacaagg tcaacaagaa gctgggttcg gccgctccgc tggacgcggg cgtcctgacg    960
gtcgaggacg tcatcgcctc gatcaagtac ctggtgaagc tgcacgccgg tgagaccgag   1020
accgtcgggg acaacggcca gtccgtggtc gtcgagaccg acgacatcga ccacttcggc   1080
aaccgccgta tccgtaacgt cggcgagctg atccagaacc aggtccgcac gggtctggcc   1140
cgtatggagc gcgtcgtgcg tgagcgcatg acgactcagg acgtcgaggc gatcacgccg   1200
cagaccctga tcaacatccg gccggtcgtc gcctccatca aggagttctt cggcaccagc   1260
cagctgtcgc agttcatgga ccagacgaac ccgctgtcgg gtctgaccca caagcgccgt   1320
ctgaacgcgc tcggccccgg tggtctctcc cgtgagcggg cgggcttcga ggtccgtgac   1380
gtgcacccgt cgcactacgg ccgcatgtgc ccgatcgaga cgcccgaagg cccgaacatc   1440
ggtctgatcg gctcgctcgc ctcgtacggc cgggtcaacg cgttcggttt catcgagacc   1500
ccgtaccgca aggtcgtcga cggtgtcgtc accgacgacg tcgactacct gacggccgat   1560
gaagaggacc gcttcgtcat cgcgcaggcc aacgccccgc tcgcggacga cctgcgcttc   1620
gccgagaacc gcgtcctggt ccgccgccgt ggcggcgagg tcgactacat ccccggcgac   1680
gacgtcgact acatggacgt ctcaccgcgc cagatggtgt cggtcgcgac cgcgatgatc   1740
cccttcctcg agcacgacga cgccaaccgc gcgctcatgg gctcgaacat gatgcgccag   1800
gccgtgccgc tgatcaaggc ggagtccccg ctggtcggca ccggcatgga gtaccgctgt   1860
gcggtcgacg ccggcgacgt catcaaggcc gagaaggacg tgtcgtccca ggaggtctcc   1920
gccgactacg tgacggtggc caacgacgac ggcacctaca ccacctaccg ggtggccaag   1980
ttctcccgct ccaaccaggg cacctccttc aaccagaagg tcgtcgtgga cgagggtgcg   2040
cgggtgatcg ccgccaggt gctggccgac ggcccgtcca ccgaggacgg cgagatggcg   2100
ctcggcaaga acctcctggt ggcgttcatg ccgtgggagg ccacaacta cgaggacgcg   2160 atcatcctca gccagcgtct ggtgcaggac gacgtcctct cctcgatcca catcgaggag   2220
cacgaggtcg atgcccgtga caccaagctc ggccccgagg agatcacccg ggacatcccg   2280
aacgtctccg aggaggtcct cgccgacctc gacgagcgcg gcatcatccg gatcggtgcc   2340
gaggtcgtcg ccggcgacat cctggtcggc aaggtcaccc gaagggcga gaccgagctg   2400 accccggagg agcggctgct gcgcgcgatc ttcggtgaga aggcccgtga ggtccgtgac   2460
acctcgctga aggtgccgca cggtgagatc ggcaaggtca tcggcgtccg cgtcttcgac   2520
cgcgaagagg cgacgaacct gccgccgggc gtgaaccagc tggtccgcgt ctacgtggcg   2580
cagaagcgca agatcaccga tggtgacaag ctcgccggcc gtcacggcaa caaggcgtc   2640 atctccaaga tcctgccggt cgaggacatg ccgttcctgg aggacggcac cccggtcgac   2700
atcatcctca acccgctggg tgtcccgtcc cgaatgaacc cggacaggt cctggagatc   2760 cacctgggct ggctggcctc ccgcggctgg aaggtcgagg gctccgagga ctggatgcag   2820
```

SEQUENCE LISTING

```
cggctccagg ccatcggcgc cgacgaggtc gagcccggca ccaacgtcgc gacccaggtc   2880
ttcgacggcg cccgcgagga cgagatcgcc ggtctcttcg actcgacgat cccgaaccgc   2940
gacggcgacc gcctggtcca gtcgtccggc aaggcccggc tcttcgacgg ccgctccggc   3000
gagccgttcc cggagccgat ctcggtcggc tacatgtaca tcctcaagct gcaccacctg   3060
gtggacgaca agctgcacgc ccggtccacc ggtccgtact cgatgatcac ccagcagccg   3120
ctgggtggta aggctcagtt cggtggccag cgcttcggtg agatggaggt gtgggcgctg   3180
gaggcttatg cgccgcgta cgccctccag gagctgctga ccatcaagtc cgacgacgtg    3240
accggccgcg tgaaggtcta cgaggccatc gtcaagggcg agaacattcc cgagcccggc   3300
atccccgagt ccttcaaggt gctcatcaag gagatgcagt ccctgtgcct caacgtggag   3360
gtgctgtcgt ccgacggcat gtccatcgag atgcgcgaca ccgacgagga cgtcttccgc   3420
gctgcggagg agctcggtat cgacctgtcc cggcgcgagc cgagcagcgt cgaagaggtc   3480
tga                                                                3483

SEQ ID NO 9
gtgctgtgcc agaaagggcg cttcgtggcc gattccggca accccatcga aaacatcccg     60
tccacgcccg acgacgaggc cctggctccg ccgtcgtacg acgccagtgc gattaccgtc    120
ctggaagggc tggaggcggt ccgcaagcga cccggtatgt acatcggttc caccggtgag    180
cgcggcctgc accatctcgt ccaagaggtc gtcgacaact ccgtcgacga ggccatggcc    240
ggtcacgcgg acagcatcga ggtcacgatc ctcgccgacg gcggcgtccg cgtcgtggac    300
aacggccgcg ggatcccggt gggcatcgtc ccctcggagg ggaagccggc tgtggaggtc    360
gtgctgaccg tgctgcacgc gggcggcaag ttcggcggcg gcggctacgc cgtctccggc    420
ggtctgcacg gcgtcggcgt ctccgtcgtc aacgccctgt cctcgaaggt gtcggtcgag    480
gtcaagacgg acggctaccg ctggaccag gactacaaga cgggagcgcc gaccgcgccc    540
ctggcccgga acgaggccac ggaggagacc ggcaccacgg tcaccttctg gcggacccg     600 gacgtcttcg agaccaccga gtactccttc gagacgctgg cccggcgctt ccaggagatg    660
gcgttcctca acaagggcct gtcgatctcg ctcaaggacg agcgcgaggc ccatgtggac    720
gaggagggca gccgctctc cgtgaagtac cactacgagg gcggcatcgt cgacttcgtg     780
acctacctca actcccgcaa gggcgagctg gtccacccca cggtgatcgg gttcgaggcc    840
gaggacaagg agcggatgct ctccctcgag atcgcgatgc agtggaacac ccagtacacc    900
gagggtgtct acagcttcgc gaacaccatc cacacccatg agggcggcac ccacgaggag    960
ggcttccgcg ccgcgctgac gtacctgatc aacaagtacg cgcgcgacaa gaagctgctc   1020
cgggagcgtg acgacaacct caccggtgag gacatccgcg agggcctgac cgccatcatc   1080
tcggtcaagc tgggcgagcc gcagttcgag ggccagacca agaccaagct gggcaacacg   1140
gaggccaaga ccttcgtcca gaagatcgtc aacgagcatc tcgccgactg gctgaccgt    1200 aaccctaatg aggcggcgga catcgtccgc aaggggatcc aggcggcgac ggcccgggtc   1260 gcggccgta aggcgcggga tctgacccgc cgtaaggggc tgctggagac cgcgtcgctg    1320
ccgggcaagc tgagcgactg ccagtccaat gacccgtcga gtgcgagat cttcatcgtc    1380 gagggtgact ccgccggcgg ctcggccaag tccggccgta acccgcagta tcaggcgatc   1440
ctcccgatcc gcggcaagat cctcaacgtg gagaaggccc gggtcgacaa gatcctgcag    1500
aacaacgagg tccaggcgct gatctccgcc ttcggcaccg gggtgcacga ggacttcgac   1560
```

| SEQUENCE LISTING | |
|---|---|
| atcgccaagc tccgctatca caagatcatt ctgatggcgg acgccgatgt cgacggccag | 1620 |
| cacatcaaca ccctgctgct gaccttcctc ttccgcttca tgcgcccgct ggtcgaggcg | 1680 |
| gggcatgtct tcctctcccg tccgccgctc tacaagatca agtggggccg ggacgacttc | 1740 |
| gagtacgcgt actcggaccg ggagcgggac gcgctgatcc aggtcggccg tgaacagggc | 1800 |
| aagcgcatca gggacgactc ggtccagcgc ttcaagggtc tgggcgagat gaacgccgaa | 1860 |
| gagctgcggg tcaccacgat ggaccccgac caccgcgtcc tgggccaggt caccctggac | 1920 |
| gacgcggcgc aggccgacga cctgttctcg gtcctgatgg gtgaggacgt cgaggcacgg | 1980 |
| cgctcgttca tccagcgcaa cgccaaggat gtccgcttcc tcgacatctg a | 2031 |
| | SEQ ID NO 10 |
| ggcgatcggc cgaacgagcc ggtcgaggtc atccccaccg ggtcgaccgc tctcgacgtc | 60 |
| gccctcggcg tcggcggtct gccgcgcggc cgggtggtcg aggtctacgg ccccgagtcc | 120 |
| tccggtaaga cgaccctgac cctgcacgcg gtggccaatg cccagcgggc cggcggcacc | 180 |
| gttgccttcg tggacgccga gcacgccctc gaccctgact acgcgcagaa gctgggcgtg | 240 |
| gacaccgact ccctgatcct gtcccagccg acaacggcg agcaggcgct cgagatcgtg | 300 |
| gacatgctgg tccgctccgg cgccctcgac ctcatcgtca tcgactccgt cgccgccctg | 360 |
| gtgccgcgcg cggagatcga gggcgagatg ggcgactccc acgtcggcct ccaggccgg | 420 |
| ctgatgagcc aggcgctccg taagatcacc agcgcgctca accagtccaa gaccaccgcg | 480 |
| atcttcatca accagctccg cgagaagatc ggcgtgatgt tcggctcgcc ggagaccacg | 540 |
| accggtggcc gggcgctgaa gttctacgcg tcggtgcgca tcgacatccg ccgcatcgag | 600 |
| accctcaagg acggcaccga cgcggtcggc aaccgcaccc gcgtcaaggt cgtcaagaac | 660 |
| aaggtcgcgc cgcccttcaa gcaggccgag ttcgacatcc tctacggcca gggcatcagc | 720 |
| cgtgagggcg gtctgatcga catgggcgtc gagcacggct tcgtccgcaa gtccggtgcc | 780 |
| tggtacacct acgagggcga ccagctcggc cagggcaagg agaacgcccg caacttcctg | 840 |
| aaggacaacc ccgatctcgc caatgagatc gagaagaaga tcaaggaaaa gctcggcatc | 900 |
| ggggtgaggc cccaggaccc ggcggccgcg gcacccacca cggacgcggc tggtgccgcg | 960 |
| ggcgtgaccg acgccgcacc ggcgaaggcc | 990 |
| | SEQ ID NO 11 |
| gtgcccagcg ccgagggcta tttcggcgcc ttcggcggca agttcatccc cgaggcgctc | 60 |
| gtcgccgccg tcgacgaggt cgcggccgag tacgagaagg ccaagacgga ccccgccttc | 120 |
| gcggccgagc tcgaggatct gctggtcaac tacaccggcc ggcccagtgc gctgaccgag | 180 |
| gtgcggcggt tcgccgagca cgccggggggc gcccgggtct tcctcaagcg ggaggacctc | 240 |
| aaccacaccg gctcccacaa gatcaacaat gtgctggggc aggccctgct caccaagcgc | 300 |
| atgggcaagt cccgggtcat cgccgagacc ggcgccggtc agcacggcgt ggccacggcc | 360 |
| accgcatgtg cgctgttcgg gctcgaatgc accatctaca tgggcgaggt cgacacccag | 420 |
| cggcaggcgc tcaatgtggc gcggatgcgg atgctgggcg ccgaggtcat ctccgtgacc | 480 |
| tccggcagcc gcaccctgaa ggacgccatc aacgaggcgt tccgggactg ggtcgccaat | 540 |
| gtggaccgca cccactacct cttcggtacg gtggccggcc cccacccctt cccggcgctg | 600 |
| gtgcgcgact ccaccggggt gatcggcgtg gaggcgcgcg ggcagatcct ggagcggacc | 660 |
| gggcggctgc cggacgcggt cgcggcctgt gtggcggcg atccaacgc gatcgggctg | 720 |
| ttccacgcct tcctgccgga cgagagcgtg cgcctcgtcg gcttcgagcc cgccggacac | 780 |

```
ggtgtggaga ccggggagca cgcggccacg ctgagccagg gcgagcccgg gatcctgcac    840
ggctcccggt cgttcgtgct ccaggacgag gacggccaga tcaccgagcc gtactcgatc    900
tcggccggtc tcgactaccc cggcgtcggg ccggagcacg cgtatctgaa ggacatcggc    960
cgtgccgagt accgggcggt caccgacgac gaggcgatgc gggcgctgcg gctgctctcg   1020
gagaccgagg gcatcatccc ggcgatcgag agcgcccacg cgctggcggg cgccctggac   1080
ctcggccgtg agctggggag cgacggcctg gtgctggtca acctctccgg gcgcggcgac   1140
aaggacatgg acacggcggc tcggtacttc gggctctacg accagcagag cgaccaggga   1200
gcgaagtga                                                          1209
                                                      SEQ ID NO 12
gtggcctccg gccgcgtcgc gcgggtcatc ggcccggtcg tcgacgtgga gttccccgtc     60
gacgcgatgc cggagatcta caacgcgctg caggtcgagg tcgccgaccc ctcccaggag    120
ggggcgaaga agaccctgac cctcgaggtc gcccagcacc tcggcgaggg cctggtccgc    180
gccatctcca tggagcccac cgacggcctg gtccgccagg ccgcggtgac cgacaccggc    240
gacggcatca cggtgccggt cggcgatgtc accaagggcc gggtgttcaa cccctcggc    300
aagatcctca cgagcccga ggccgagtcc gaggtcaccg agcgctggtc catccaccgc    360
aaggcccgg ccttcgacca gctcgagtcc aagaccgaga tgttcgagac cggcctgaag   420
gtcgtcgacc tgctgacccc gtacgtcaag ggcggcaaga tcggtctgtt cggcggcgcg    480
ggcgtcggca agaccgtgct catccaggaa atgatcatgc gtgtggccaa gctgcacgag    540
ggcgtttccg tgttcgccgg tgtcggcgag cgcacccgtg agggcaacga cctgatcgag    600
gagatggccg agtccggcgt gctcccgcag accgcgctgg tcttcggcca gatggatgag    660
ccccgggca cccgtctgcg cgtcgccctg gccggtctga ccatggcgga gtacttccgc    720
gatgtgcaga gcaggacgt gctgttcttc atcgacaaca tcttccgctt cacccaggcc    780
ggttccgagg tctcgaccct gctcggccgg atgccctccg cggtgggcta ccagccgaac    840
ctggccgacg agatgggcat cctgcaggag cgcatcacct cgacccgtgg tcactcgatc    900
acctcgatgc aggcgatcta cgtccccgcg gacgacctga ccgacccggc cccggcgacc    960
accttcgcgc acctcgacgc gaccacggtg ctctccccgg cgatctcgga gaagggcatc   1020
taccccggcgg tggacccgct ggactcgacg tcccggatcc tggacccgcg ctacatctcg   1080
caggagcact acgactgcgc ctcgcgcgtg aagtcgatcc tgcagaagta caaggacctc   1140
caggacatca tcaacatcct gggcatcgac gagctcggcg aggaggacaa gctcaccgtc   1200
ttccgcgccc gccggatcga gcgcttcctg tcgcagaaca cccacgcggc gaagcagttc   1260
accggcctcg acgatcgga tgtgccgctg gacgagtcca tcgccgcgtt caacgcgatc   1320
gccgatggtg agttcgacca cttccccgag caggcgttct tcatgtgcgg tggcctggac   1380
gacctcaagg ccaaggccaa ggagctgggc gtctcctga                         1419
```

The invention claimed is:

1. A method for treating plant material, comprising applying to the plant material a composition comprising at least one biological agent selected from:
   bacteria of the genus *Streptomyces* comprising a 16S rDNA, which codes for the 16S ribosomal RNA of said bacteria and is 100% homologous with SEQ ID NO: 1; and
   culture media in which bacteria comprising the 16S rDNA sequence that is 100% homologous with SEQ ID NO: 1 have developed and which are free of said bacteria, said culture media comprising polynucleotides having a DNA sequence that is 100% homologous with SEQ ID NO: 1,
   and wherein the bacteria are selected from the group consisting of:
   bacteria corresponding to the strain deposited and registered on 7 Apr. 2011 under number 1-4467 with the National Collection of Microorganisms Cultures (CNCM) of the Pasteur Institute; and
   mutant bacteria of the deposited strain, obtained by mutagenesis of bacteria of the strain deposited and registered on 7 Apr. 2011 under number 1-4467 with the National Collection of Microorganisms Cultures (CNCM) of the Pasteur Institute, said mutant comprising the 16S rDNA sequence that is 100% homologous with SEQ ID NO: 1, said mutant bacteria being capable of inhibiting the growth of phytopathogenic target microorganisms.

2. The method according to claim 1, wherein the plant material is selected from the group consisting of all or part of a plant in cultivation, of a fruit or vegetable after harvesting, and of seeds and propagating material of plants.

3. The method according to claim 1, wherein a treatment composition further comprising a solid nutriment in the divided state is used.

4. The method according to claim 1, wherein said treatment composition is applied to said plant material in order to activate the growth thereof.

5. The method according to claim 1, wherein said treatment composition is applied to said plant material in order to inhibit the growth of at least one target microorganism.

6. The method according to claim 1, wherein said treatment composition is applied to said plant material in order to stimulate the natural defenses of said plant material.

7. The method according to claim 1, wherein the composition is liquid.

8. The method according to claim 1, wherein the composition is solid.

9. The method according to claim 1, wherein the composition comprises at least one acceptable excipient for permitting its application to plant material to be treated.

10. The method according to claim 1, for treating agricultural plant crops, comprising applying to plants or seeds of said agricultural plant crops an effective amount of the composition.

11. The method according to claim 1, wherein the composition is applied to plants for stimulating the growth of plants.

12. The method according to claim 1, wherein the composition is applied to seeds for stimulating the germination of seeds.

13. The method according to claim 1, wherein the composition is applied to plants for a fertilization treatment of plants.

14. The method according to claim 1, wherein the composition is applied to plants for an antimicrobial and/or antiviral treatment of plants.

15. The method according to claim 1, wherein the composition is applied to plants for stimulating the natural defenses of plants.

16. The method according to claim 1, wherein the bacteria are the strain deposited and registered on 7 Apr. 2011 under number 1-4467 with the National Collection of Microorganisms Cultures (CNCM) of the Pasteur Institute.

* * * * *